US012714110B2

(12) United States Patent
McKernan et al.

(10) Patent No.: US 12,714,110 B2
(45) Date of Patent: Aug. 25, 2026

(54) MATERIALS AND METHODS FOR DETECTING PATHOGEN LOAD

(71) Applicant: Medicinal Genomics, Beverly, MA (US)

(72) Inventors: Kevin McKernan, Marblehead, MA (US); Biao Liu, Lexington, MA (US)

(73) Assignee: Medicinal Genomics, Beverly, MA (US)

( * ) Notice: Subject to any disclaimer, the term of this patent is extended or adjusted under 35 U.S.C. 154(b) by 0 days.

(21) Appl. No.: 17/755,687

(22) PCT Filed: Nov. 5, 2020

(86) PCT No.: PCT/US2020/059207
§ 371 (c)(1),
(2) Date: May 5, 2022

(87) PCT Pub. No.: WO2021/092245
PCT Pub. Date: May 14, 2021

(65) Prior Publication Data

US 2022/0369649 A1 Nov. 24, 2022

Related U.S. Application Data

(60) Provisional application No. 62/951,820, filed on Dec. 20, 2019, provisional application No. 62/931,680, filed on Nov. 6, 2019.

(51) Int. Cl.

| | |
|---|---|
| ***C12N 15/80*** | (2006.01) |
| ***A01N 63/50*** | (2020.01) |
| ***C07K 14/415*** | (2006.01) |
| ***C12N 9/42*** | (2006.01) |
| ***C12N 15/10*** | (2006.01) |

(52) U.S. Cl.
CPC ............ *A01N 63/50* (2020.01); *C07K 14/415* (2013.01); *C12N 9/2442* (2013.01); *C12N 15/1003* (2013.01); *C12Y 302/01014* (2013.01)

(58) Field of Classification Search
None
See application file for complete search history.

(56) References Cited

U.S. PATENT DOCUMENTS 6,512,166 B1 * 1/2003 Harman ......... C12Y 302/01014 514/3.3
9,848,603 B2 12/2017 Anderson et al.
2013/0095524 A1 4/2013 Yokoyama et al.
2016/0273055 A1 * 9/2016 Mills .................... C12Q 1/6895
2017/0295797 A1 10/2017 Curtis et al.

FOREIGN PATENT DOCUMENTS

WO 2011009992 A2 1/2011

OTHER PUBLICATIONS

Ribeiro Quintas (PhD thesis, The university of British Columbia, Canada, published Oct. 2019).*
Decuyper et al. (European Journal of allergy and clinical immunology, 73(9): 1911-1914, 2018).*
Punja et al. (Frontiers in Plant Science, 10:1-23, 2018).*
Genbank1 (Sequence Accession No. XP_030498517, Published Aug. 28, 2019).*
Genbank2 (Sequence Accession No. XP_030639569.1, Published Aug. 28, 2019).*
Ebadzad et al. (Springer Plus, 3 (613): 1-13, Published 2014).*
Adrangi et al. (Biotechnology Advances, 31:1786-1795.*
Hon et al. (Plant Physiology, 109:879-889, 1995).*
Liu et al. (Plant Cell Reports, 29:419-436, 2010).*
Palacin et al. (Clinical and Experimental Allergy, 40:1422-1430, 2010).*
Ribeiro Quintans, I. "Molecular Responses of Plants to Symbiotic Fungi," University of British Columbia, Oct. 31, 2019 (Oct. 31, 2019), pp. 1-210 (only pp. 1-5, 28-63 provided). Retrieved from the Internet: <URL: https://open.library.ubc.ca/clRcle/collections/ubctheses/24/items/1.0384823> on Feb. 3, 2021 (Feb. 3, 2021). Entire document.
Decuyper, I. I. "Cannabis Allergy & Associated Food Allergies: Exploring their True Colors," Universiteit Antwerpen, Mar. 15, 2019 (Mar. 15, 2019), pp. 1-209 (only pp. 1-32 provided). Retrieved from the Internet <URL: https://repository.uantwerpen.be/docman/irua/29b146/14515.pdf> on Feb. 3, 2021 (Feb. 3, 2021). Entire document.
Punja et al. "Pathogens and Molds Affecting Production and Quality of *Cannabis sativa* L.," Frontiers in Plant Science, Oct. 17, 2019 (Oct. 17, 2019), vol. 10, No. 1120, pp. 1-23. Entire document.
Neeraja et al. "Biotechnological approaches to develop bacterial chitinases as a bioshield against fungal diseases of plants," Critical Reviews in Biotechnology, Jun. 24, 2010 (Jun. 24, 2010) vol. 30, Issue 3, pp. 231-241 (only pp. 1-32 provided).

* cited by examiner

*Primary Examiner* — Vinod Kumar
(74) *Attorney, Agent, or Firm* — MH2 Technology Law Group, LLP

(57) ABSTRACT

This invention generally relates to compositions comprising thaumatin-like proteins (TLP) and chitinases for use as laboratory reagents or biofungicides. The invention further relates to methods of detecting and inducing pathogen resistance in plants.

13 Claims, 9 Drawing Sheets

Specification includes a Sequence Listing.

MIQNNCGRTIWPATQSGSGSSQLSTTGFELASGASQSIEIPAGPWSGRFWGRDGCSTDSSGRFACAS
GDCASGTVECNGAGGVPPTTLVEITVAENGGQDFYDVSNVDGFNLPVSVRPE
GGNGDCQESTCPNNLNDGCPADLQYKSGDDVVGCLSSCAKYNMDQDCCRGAYDSPDTCTPSESANYF
EQQCPQAYSYAYDDKTSTFTCSGGPNYLITFCPHHHHHH

FIG. 8

MATERIALS AND METHODS FOR DETECTING PATHOGEN LOAD

CLAIM OF PRIORITY

The present application is a U.S. National Stage entry under U.S.C. 371 of International Application No. PCT/US2020/059207, filed on Nov. 5, 2020, designating the United States of America and published in English on May 14, 2021, which in turn claims priority to U.S. Provisional Application No. 62/931,680 entitled "DETECTING AND INDUCING PATHOGEN RESISTANCE," filed Nov. 6, 2019 and U.S. Provisional Application No. 62/951,820, entitled "DETECTING AND INDUCTING PATHOGEN RESISTANCE," filed Dec. 20, 2019, the entire contents of each of the foregoing are hereby expressly incorporated by reference herein.

REFERENCE TO AN ELECTRONIC SEQUENCE LISTING

The contents of the electronic sequence listing (2024-03-21-Corrected Sequence Listing_ST25-MGEN-001US0.xml; Size: 35,943 bytes; and Date of Creation: Mar. 11, 2024) is herein incorporated by reference in its entirety.

BACKGROUND

Field

This invention generally relates to compositions comprising thaumatin-like proteins (TLP) and chitinases for use as laboratory reagents or biofungicides. The invention further relates to methods of detecting and inducing pathogen resistance in plants.

BACKGROUND

*Cannabis sativa* L. is one of the earliest domesticated plants. Classified independently by Linnaeus and Lamarck, hemp fiber was used by Marco Polo and James Cook for rope, sails, paper, and ship caulk. The extensive maritime use of *Cannabis* has played a role in its spread around the globe, creating an interesting admixture of landrace genetics. The suitability of the common subspecies vernacular of *Cannabis sativa*, subsp. *sativa* indica, and *ruderalis* has been hotly debated but infrequently verified with genomic surveys. Segregation of fiber based *Cannabis* (hemp) and drug type *Cannabis* (sometimes referred to as marijuana) has been genetically resolved[21-28]. Hemp genetics are ancestral and often produce distinct male and female flowers on a single plant (monoecious). Dioecious *Cannabis* can be hermaphroditic but this usually entails bisexual flowers that are distinct from flowers found on monoecious phenotypes. Drug type *Cannabis* has undergone selection for female flowers that produce high levels of tetrahydrocannabinolic acid (THCA). This selection has produced predominantly dioecious female varieties for modern cannabinoid production [29,30].

*Cannabis* is diploid and has 10 chromosomes (2n=20) and an XY sex chromosome system[31]. While dioecious genetics are preferred for cannabinoid production, hermaphroditic traits still circulate in the drug type varieties, complicating mass production of cannabinoids. Since pollinated female flowers produce lower levels of cannabinoids and terpenes, male drug type plants are visually or genetically tested and culled from grows to prevent pollination of female plants. Visual sexual differentiation occurs in the midlife cycle of the plant, while genetic screening can eliminate males earlier to conserve expensive indoor growing real estate. Female plants with hermaphroditic tendencies are more difficult to detect and remove using visual or genetic screening methods.

To avoid the propagation of Y chromosomes in naturally-crossed *Cannabis* seeds, indoor growers often resort to tissue culture or cloning of female mother plants. This can lead to monocultures and increased risks associated with pathogen exposure (Wally and Punja 2010). Another approach more common in outdoor cannabidiolic acid (CBDA) production utilizes the induction of hermaphroditism with silver nitrate and ethephon treatment (an ethylene blocker and ethylene mimetic respectively). These phytohormone modulators reverse the sex phenotype of some female and male varietiesvarieties respectively. Only sex reversal of female plants with silver nitrate results in pure XX pollen production (Mohan Ram and Sett 1982). Application of XX pollen to female flowers results in 'feminized' seeds but can also increase the incidence of plants with hermaphroditic capacity. The hermaphroditic capacity of varieties is believed to be a heritable trait but this trait has yet to be mapped to any genomic coordinates. Sex chromosomes in flowering plants usually evolve from autosomes (Harkess et al. 2016; Harkess et al. 2017). Likewise, modern monoecious hemp varieties tend to decay into dioecious varieties with inbreeding but little is known about their chromosomal structures (Clarke 2017).

Cannabinoid and terpene production by plants is linked to both attraction of pollinators and responses to plant pathogens (Penuelas et al. 2014; Andre et al. 2016; Allen et al. 2019) (Lyu et al. 2019). Despite successful breeding efforts to deliver higher cannabinoid and terpene contents, plant pathogens are still a significant contributor to crop loss in *Cannabis* production due to the lack of disease-resistant varieties (Kusari 2013; Backer et al. 2019). Many jurisdictions mandate *Cannabis* microbial safety testing targeting epiphytic and endophytic plant pathogens that have been clinically linked to Aspergillosis in immuno-compromised *Cannabis* patients.

*Cannabis*-derived powdery mildew can result in significant crop loss with outdoor and indoor *Cannabis* cultivation. The CDC and OSHA have reported high spore exposure risk in *Cannabis* trimming environments that have led to Powdery mildew induced allergies[1, 2].

Many *Cannabis* varieties are believed to be powdery mildew resistant but the genetics governing this trait have not been discovered yet. Identification of this gene can lead to more targeted breeding, increased yields, and reduced employee allergen exposure. Cloning and expression of the genes can enable foliar enzymatic sprays for epiphytic pathogens. Hemp transformations with *agrobacterium* have also been described in the literature suggesting more directed integration of resistance alleles is possible[3].

In most states, inhalable herbs such as *Cannabis* must be tested for microbial contamination. This can be difficult to do with cell culture or plating as many of the fungi are endophytes. As a result of their endophytic nature, plant cell walls need to be lysed to access the fungi and the conditions required to lyse open plant cell walls may partially or fully lyse open microbial cell walls.

SUMMARY

Some embodiments of the invention relate to a method of determining microbial burden in a plant. The method can include obtaining a plant sample and applying a composition to the plant sample. The composition can include an active chitinase and an active thaumatin-like protein (TLP). The method can include extracting gDNA or RNA from the plant sample and detecting genes associated with microbial burden from the gDNA or RNA. In some embodiments, the presence of genes associated with microbial burden is indicative of microbial burden.

In some embodiments, the chitinase is derived from *Cannabis*. In some embodiments, the TLP is derived from *Cannabis*.

In some embodiments, the plant is a *Cannabis* plant.

Some embodiments of the invention relate to a composition including a first enzyme and a second enzyme wherein the first enzyme can be a chitinase and the second enzyme can be glucanase, mannase, or endo-1,2C4-beta-mannosidase. In some embodiments, the first and second enzyme are in a concentration effective for lysis of fungal cell walls.

In some embodiments, the composition can be in the form of a foliar spray.

In some embodiments, the composition can be in the form of a laboratory agent.

Some embodiments of the invention relate to a method of treating or preventing pathogen infection in a plant using the foliar spray.

Some embodiments of the invention relate to a method of isolating a nucleic acid using the laboratory reagent.

Some embodiments of the invention relate to a recombinant organism that can express a thaumatin-like protein (TLP) and/or chitinase gene capable of acting as a biofungicide on a plant.

In some embodiments, the TLP can be CsTLP1.

In some embodiments, the recombinant organism can be *E. coli, Bacillus subtilis, Saccharomyces cerevisiae*, or *A. tumefaciens*.

Some embodiments of the invention relate to a method of treating or preventing pathogen infection in a plant using the recombinant organism.

BRIEF DESCRIPTION OF THE DRAWINGS

FIG. 8 depicts pET-30a (+) expression of CsTLP1 in *E. coli* grown in TB. Nicole purified 6× His Tag and eluted in 20 Mm Tris-HCl, 500 mM NaCl, 10 mM GSH, 1 mM GSSG, 20% Glycerol, pH 7.5. The N terminal Signal peptide was removed and a 6× His Tag added to the C terminus. Critical Cysteine residues are highlighted in grey.

DETAILED DESCRIPTION

Compositions Including TLP and Chitinase

Figure 1:
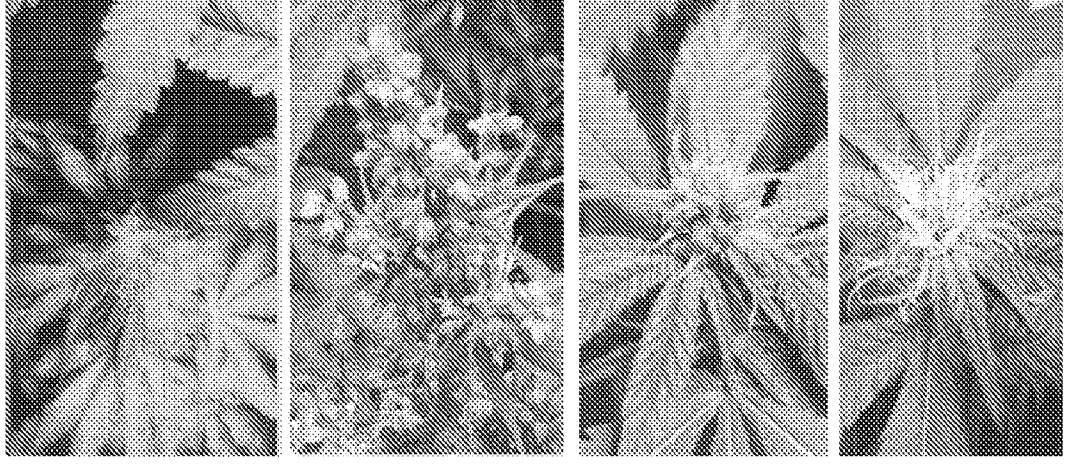
FIG. 1 contains photographs of plants in experiments: (left) Attempted inoculation of Jamaican Lion mother clone with *G. chicoracearum*. (middle-left) Male *G. chicoracearum*-susceptible variety. (middle-right) Jamaican Lion mother clone treated with silver nitrate to induce hermaphroditic female flowers. (right) Non-treated Jamaican Lion mother flower (XX).

The invention provides compositions and methods using thaumatin-like proteins (TLPs) and Chitinases in compositions as laboratory reagents. In some examples, the invention can be used for isolating DNA from difficult-to-lyse fungi. *C. albicans* and *S. cerevisiae* are known to have thick glucan and chitin cell walls and the ratio of glucan and chitin can shift throughout its life cycle (Ruiz-Herrera et al. 2006; Lee et al. 2012; Cottier et al. 2019; Garcia-Rubio et al. 2019).

The present disclosure recognizes that enzymes derived from fungal resistant *Cannabis* are ideally evolved to lyse open fungi that are known to infect non-resistant *Cannabis*. These *Cannabis* enzymes can be used to lyse samples being prepared for microbial quantification in the *Cannabis* microbial detection assays.

Glucanases (e.g., lyticase) are used for lysis of microbial walls (Fredricks et al. 2005; Goldschmidt et al. 2014; Fraczek et al. 2019) but glucanases alone may not fully dissolve fungal cells walls comprised of both glucan and chitin. To fully survey the endophytic fraction of fungi in *Cannabis* one needs to pay close attention to fungal cell wall variance in the population and design lysis conditions that can quantitatively lyse a diversity of organisms. Organisms like *S. cerevisiae* and *C. albicans* have not been reported as pathogen of *Cannabis* yet but they are reported as excellent model organisms known to have difficult-to-lyse cell walls.

Compositions for lysing microbial walls are provided. The compositions can include a first enzyme and a second enzyme. The first enzyme can be an active chitinase or related enzyme. The second enzyme is can be glucanase, mannase, endo-1,2C4-beta-mannosidase or the like. The concentrations of the enzymes are in a concentration effective for lysis of microbial cell walls. The first enzyme can be in a concentration of about 5, 10, 15, 20, 25% of the composition. The second enzyme can be in a concentration of about 5, 10, 15, 20, 25% or more of the composition. In some embodiments, the enzymes have a synergistic effect.

The method described herein comprises: providing a sample or suspension for evaluation of possible microbial contamination; producing a sample-lysing composition by adding to the sample a mixture of lysing enzymes; and incubating the sample for sufficient time and at a temperature to produce a lysed microbial sample and thereby allow the release of microbial nucleic acids. Further still, purified nucleic acids can be detected and/or analyzed by any conventional detection technique.

By "suspension" is meant a sample in which particulates are suspended in a liquid and can include, but is not limited to, cell suspensions, or tissue homogenates wherein tissue samples are macerated into aqueous buffers, or suspensions of particulates such as chromatography support material in aqueous buffer solutions.

The sample can be centrifuged and resuspended in a solution. The mixture of lysing enzymes is then added and the sample is incubated for a sufficient time and at a sufficient temperature to produce a lysed microbial cell sample wherein the microbial nucleic acids have been released from the microbial cells. In one embodiment, the mixture of lysing enzymes can include at least one enzyme selected from a chitinase or related enzyme, and at least one enzyme selected from glucanase, mannase, endo-1,2C4-beta-mannosidase or the like. In a further preferred embodiment, the sample is incubated for 10 to 60 minutes at a temperature between about 25° C. and 37° C. The method described herein can include the further step of isolating released microbial nucleic acid using methods known in the art such as binding of the released microbial nucleic acid to a nucleic-acid binding support (see for example Medicinal Genomics part #420001 SenSATIVAx, MagAttract DNA or EZ-1 DNA kits by Qiagen, or the Mag DNA Isolation kits by Agowa). Preferably, isolated microbial nucleic acids can then be detected or analyzed using any conventional detection technique known in the art, e.g. amplification techniques such as PCR, TMA, NASBA, RT-PCR, optionally followed by sequence analysis if desired.

By "lysing enzyme" is meant any of a number of well-known enzymes that act to digest components of microbial cell walls, thus causing the cell to be disrupted or lyse. Examples of lysing enzymes include, but are not limited to, lyticases, chitinases, zymolases, gluculases, lysozymes, lysostaphins, and mutanolysins. All of these enzymes are well known and readily available from a variety of commercial sources.

In another aspect, the present invention provides a method for microbial cell disruption to allow release of nucleic acid from microbial cells present in a sample as defined in the claims comprising: providing a sample containing or suspected of containing microbial cells, wherein the sample is a sample or suspension, and producing a sample-lysing composition by adding to the sample a mixture of lysing enzymes, and incubating the sample for sufficient time and at a temperature to produce a lysed microbial sample and thereby to allow the release of the microbial nucleic acids.

In some embodiments, the method comprises: providing a sample or suspension containing or suspected of containing microbial cells; producing a sample-lysing composition by adding to the sample a mixture of lysing enzymes; and incubating the sample for sufficient time and at a temperature to produce a lysed microbial sample and thereby to allow the release of microbial nucleic acids.

The method can include: providing a sample or suspension containing or suspected of containing microbial cells; producing a sample-lysing composition by adding to the sample a mixture of lysing enzymes, wherein the mixture of lysing enzymes can include at least one enzyme selected from a chitinase or related enzyme, and at least one enzyme selected from glucanase, mannase, endo-1,2C4-beta-mannosidase or the like; and incubating the sample for sufficient time and at a temperature to produce a lysed microbial sample and thereby to allow the release of the microbial nucleic acids.

The incubation time and temperature conditions sufficient to produce a lysed microbial sample will be readily determined be one of ordinary skill in the art and will depend in part on the requirements of the particular lysing enzymes chosen. In general, a time of the incubation step that is about 10 to about 60 minutes, preferably between 30 and 60 minutes, at temperatures between about 25° C. and about 37° C., preferably between 30-37° C., will be suitable.

In another embodiment, the method can include: providing a sample or suspension containing or suspected of containing microbial cells; producing a sample-lysing composition by adding to the sample a mixture of lysing enzymes, wherein the mixture of lysing enzymes can include at least one enzyme selected from a chitinase or related enzyme, and at least one enzyme selected from glucanase, mannase, endo-1,2C4-beta-mannosidase or the like; and incubating the sample for between about 10 minutes and about 60 minutes and at a temperature of between about 25° C. and about 37° C. to produce a lysed microbial sample and thereby to allow the release of microbial nucleic acids.

The lysing enzymes will be present in the lysing composition and the sample-lysing composition at concentrations sufficient to achieve lysis of microbial cells present in the sample. The appropriate concentrations are readily determined by one of ordinary skill in the art and typically will range from 0.1 unit/mL to 106 units/mL. However, it will be readily apparent to one of ordinary skill in the art that parameters of enzyme concentration, incubation time and incubation temperature, are interdependent and can be adjusted in various ways to achieve the same or very similar result. For example, a lower enzyme concentration can be compensated for by a longer incubation time, a lower incubation temperature can be compensated for by a longer incubation time and/or a higher enzyme concentration.

Following protease digestion, the released nucleic acids can optionally be isolated using any convenient technique (see, e.g., U.S. Pat. Nos. 5,234,809; 6,465,639; 6,673,631; 6,027,945; 6,383,393; 5,945,525; 6,582,922, inter alia). A number of kits/reagents are available commercially for carrying out nucleic acid isolation, for example, the Medicinal Genomics part #420001 SenSATIVAx, MagAttract DNA kits or EZ-1 DNA kits from Qiagen (Valencia CA, catalogue number 953336) and the Mag DNA Isolation kits from Agowa (Berlin, Germany, catalogue number 953034). These kits utilize silica-based magnetic beads and chaotropic agents to non-specifically bind nucleic acid to the beads. Any silica membrane based methods can also be used, such as QIAamp DNA kits (Qiagen, for example catalogue numbers 51304, 51161, 51192, 51104, 52904) and Nucleospin kits (Machery-Nagel, for example catalogue numbers 740951, 740691, 740740, 740623). Other suitable kits include the Magnesil or the 96 Wizard kits (Promega, catalogue number A2250), the Nucleomag kit (Machery-Nagel, catalogue number 744500), DNA Direct kit (Dynal, catalogue number 630.06) and Magnazorb (Cortex Biochem., catalogue numbers MB1001, MB2001) The supplier's protocols are followed when using these kits except that the steps and reagents for cell-wall lysis, if any are included, are replaced by the lysis methods of the present invention.

The isolated nucleic acids can be detected and/or analyzed by any conventional detection technique, including e.g., amplification techniques such as PCR, TMA, NASBA, RT-PCR, optionally followed by sequencing analysis, if it is desirable for determination of the types, species and strains of microorganism detected. The target for amplification and detection can be one that is similar among a wide variety of microbial species (e.g., 16S RNA gene, 23S RNA gene, tuf (elongation factor Tu) gene, or any conserved housekeeping gene for bacteria or yeast) or can be one that is specific for a particular organism.

By "lysis" of a microbial cell is intended the disruption, rupture, poration, permeabilization, digestion or break down of the microbial cell wall such that the nucleic acid components of the cell can be released into the external medium. In some applications, the release of the nucleic acids into the external medium can be facilitated by the addition of detergent that acts to solubilize the cell membranes. According to the invention, the microbial cell wall need not be completely disrupted, ruptured, permeabilized or digested in order to effect the release of the nucleic acids.

By "release" of the microbial nucleic acids is intended that the microbial nucleic acids, particularly the genomic nucleic acids, are no longer retained within the cell but are free and accessible to various nucleic acid isolation procedures.

The composition can also be used as a biofungicide by lysis of microbial cell walls as described herein. In such embodiments, the composition can be in the form of a foliar spray. The spray can be used to treat or prevent pathogen infection on plants. Formulation of a spray from the lysing composition can be done by conventional means.

The microbe as disclosed herein can be any microbe described in this disclosure, for example, a fungi. In particular, the fungi can be any member of the Ascomycota such as but not limited to *Botrytis cinerea, Golovinomyces chicoracearum, Penicillium* spp., *Fusarium* spp. *Blumeria* spp., *Erisiphe* spp., and/or *Aspergillus* spp. Since TLPs and chitinases show activity against key components of the cell walls of essentially all fungi, in some embodiments, the biotroph target is any fungus capable of infecting a plant, and particularly a *Cannabis* plant.

Genes Regulating *Cannabis* Sex Evolution, Cannabinoid Expression, and Pathogen Resistance Some embodiments of the invention relate to genes regulating *Cannabis* sex evolution, cannabinoid expression and pathogen resistance. Specifically, the invention relates to thaumatin-like proteins (TLPs), chitinases and mildew resistance loci O (MLO). For example, some embodiments of the invention relate to detecting a combination of TLPs and chitinases to determine pathogen resistance, a profile of pathogen-resistant genes, or overall health of a plant. Some embodiments detect MLO to determine pathogen resistance or health of a plant. Presence of TLPs, chitinases, and/or MLO can be determined by fluorescence methods, mass spectrometry or similar methods, β-1,3-glucanase assay, detection of gene copy number, and/or detection of mRNA expression levels. For example, the TLPs and chitinases that are detected to determine pathogen resistance in a plant can be a combination of CsTLP1, chitinase_c2033, chitinase_c13, chitinase_c69 and chitinase_c87. For example, the combination can be one TLP and one chitinase.

Some embodiments of the invention relate to a quantitative PCR assay that surveys both the expression of TLP and/or chitinase RNA and genomic copy number compared to other *Cannabis* housekeeping genes to determine sex, cannabinoid expression and/or pathogen resistance. This assay can help breeders optimize plant health, trimmer PM allergen exposure and TLP allergen load. Sequences used for the assay are provided. Embodiments of the invention can use sequences with 50, 55, 60, 65, 70, 75, 80, 85, 90, 95, or 100% sequence identity to those provided.

Monitoring both RNA and DNA from CsTLP1 is augmented with qPCR detection of the Powdery mildew organism (Golovinomyces chicoracearum).

Some embodiments of the invention relate to a method of determining pathogen resistance in a plant including obtaining a sample of the plant and using a fluorescent probe to detect the nucleic acid copy number of TLPs and/or chitinases in the sample compared to an autosomal control gene. The presence of one or more resistant alleles of TLP and/or chitinase genes can be indicative of pathogen resistance.

Some embodiments of the invention relate to a method of determining the health of a plant including obtaining a sample of the plant and using Mass spectroscopy to detect TLPs and/or chitinases in the sample compared to an autosomal control protein. The presence of one or more TLPs and/or chitinases can assess the health of the plant.

Some embodiments of the invention relate to a method of determining pathogen resistance of a plant including obtaining a sample of the plant, detecting both gene copy number and mRNA expression of TLPs and/or chitinases and an autosomal control target in the plant, calculating a relative change in gene copy number and expression to calculate a PM resistance score. The PM resistance score can be correlated with pathogen resistance.

Some embodiments of the invention relate to a method of determining pathogen resistance of a plant obtaining a sample of the plant; detecting both gene copy number and mRNA expression of TLPs and/or chitinases and an autosomal control target in the plant; detecting the presence of a biotroph; calculating a relative change in gene copy number and expression and considering the presences of the biotroph to calculate a PM resistance score, wherein the PM resistance score is correlated with pathogen resistance.

Some embodiments combine detecting a combination of TLPs and chitinases to determine pathogen resistance, a profile of pathogen-resistant genes, or overall health of a plant. Some embodiments detect MLO to determine pathogen resistance or health of a plant. Presence of the genes can be determined by fluorescence methods, mass spectrometry or similar methods, β-1,3-glucanase assay, detection of gene copy number, and/or detection of mRNA expression levels. For example, the TLPs and chitinases can be a combination of CsTLP1, chitinase_c2033, chitinase_c13, chitinase_c69 and chitinase_c87.

In some embodiments, the biotroph is a member of the Ascomycota such as but not limited to *Botrytis cinerea, Golovinomyces chicoracearum, Penicillium* spp., *Fusarium* spp. *Blumeria* spp., *Erisiphe* spp., and/or *Aspergillus* spp. Since TLPs and chitinases show activity against key components of the cell walls of essentially all fungi, in some embodiments, the biotroph target is any fungus capable of infecting a plant, and particularly a *Cannabis* plant.

Some embodiments of the invention relate to a kit comprising a tube with reagents to perform any of the methods disclosed herein Kits In some embodiments, the present disclosure provides kits comprising materials useful for amplification and detection and/or sequencing of plant nucleic acid (e.g., DNA).

Suitable amplification reaction reagents that can be included in an inventive kit include, for example, one or more of: buffers; enzymes having polymerase activity; enzyme cofactors such as magnesium or manganese; salts; nicotinamide adenide dinuclease (NAD); and deoxynucleoside triphosphates (dNTPs) such as, for example, deoxyadenosine triphospate; deoxyguanosine triphosphate, deoxycytidine triphosphate and deoxythymidine triphosphate, biotinylated dNTPs, suitable for carrying out the amplification reactions.

In some embodiments, a kit comprises 1, 2, 3, 4, 5, 6, 7, 8, 9, 10, 11, 12, 13, 14, 15, 16, 17, 18, 19, 20, or more primer sequences for in vitro nucleic acid amplification. Primer sequences can be suitable for in vitro nucleic acid amplification with any of the methods described herein (e.g., QT-PCR, LAMP, etc.). In some embodiments, a kit of the present disclosure includes reagents suitable to perform a colorimetric LAMP assay for amplification of one or more gene sequences as described herein.

Depending on the procedure, a kit can further include one or more of: wash buffers and/or reagents, hybridization buffers and/or reagents, labeling buffers and/or reagents, and detection means. The buffers and/or reagents included in a kit are preferably optimized for the particular amplification/detection technique for which a kit is intended. Protocols for using these buffers and reagents for performing different steps of the procedure can also be included in a kit.

In some embodiments, a kit can further include one or more reagents for preparation of nucleic acid from a plant sample. For example, a kit can further include one or more of a lysis buffer, a DNA preparation solution (e.g., a solution for extraction and/or purification of DNA). Kits can also contain reagents for the isolation of nucleic acids from biological specimen prior to amplification. Protocols for using these reagents for performing different steps of the procedure can also be included in a kit. The lysis buffer can include any of the lysing compositions as described herein.

Furthermore, kits can be provided with an internal control as a check on the amplification procedure and to prevent occurrence of false negative test results due to failures in the amplification procedure. An optimal control sequence is selected in such a way that it will not compete with the target nucleic acid sequence in the amplification reaction.

In some embodiments, a kit can further include reagents for an amplification assay to characterize the gender of a plant or determine pathogen resistance.

Reagents can be supplied in a solid (e.g., lyophilized) or liquid form. Kits of the present disclosure can optionally comprise different containers (e.g., vial, ampoule, test tube, flask or bottle) for each individual buffer and/or reagent. In some embodiments, each component will generally be suitable as aliquoted in its respective container or provided in a concentrated form. Other containers suitable for conducting certain steps of inventive amplification/detection assay(s) can also be provided. Individual containers of a kit are preferably maintained in close confinement for commercial sale.

A kit can also include instructions for using the amplification reaction reagents, primer sets, primer/probe sets according to the present disclosure. Instructions for using a kit according to one or more methods of the present disclosure can comprise instructions for processing the biological sample, extracting nucleic acid molecules, and/or performing one or more amplification reactions; and/or instructions for interpreting results. In some embodiments, a kit can comprise instruction for determining, assessing and/or classifying a plant used in the described methods as a Type Ia, Type Ib, Type IIa, Type IIb, Type IIc, Type IIIa, Type IIIb, Type IV or Type V plant or determining pathogen resistance of the plant.

Biofungicides

Some embodiments of the invention relate to a recombinant organism expressing a TLP and/or chitinase gene capable of acting as a biofungicide on a plant. In some embodiments, the TLP is CsTLP1. In some embodiments the organism is *E. coli, Bacillus subtilis* or *Saccharomyces cerevisiae*. Some embodiments of the invention relate to a method of treating or preventing pathogen infection in a plant using the recombinant organism.

Provided are compositions including the recombinant organism in the form of a foliar spray.

Some embodiments of the invention relate to a method of treating of preventing pathogen infection in a plant using the foliar spray.

Applications

The microbes, biotrophs, pathogens as described herein in connection with the composition, kits and methods of the invention can include, but not be limited to: *Alternaria alternata; Arthrinium* species; *Aspergillus aculeatus; Aspergillus brasiliensis; Aspergillus caesiellus; Aspergillus flavus; Aspergillus fumigatus; Aspergillus niger; Aspergillus oryzae; Aspergillus terreus; Aureobasidium* species; *Botrytis cinerea; Candida albicans; Candida tropicalis; Cladosporium* species; *Cryptococcus laurentii; Cryptococcus neoformans; Erysiphe* species; *Fusarium proliferatum; Fusarium oxysporum; Fusarium solani; Golovinomyces cichoracearum; Hyphodontia* species c; *Microsphaera* species; *Mucor circinelloides; Mucor hiemalis; Paecilomyces* species; *Penicillium chrysogenum; Penicillium rubens; Penicillium venetum; Phytophthora infestans; Podosphaera* species; *Purpureocillium* species; *Rhizopus oryzae; Rhizopus stolonifera; Scopulariopsis acremonium; Sphaerotheca* species; *Yarrowia lipolytica; Talaromyces pinophilus*; and the like.

Plants that additionally can be treated according to the invention can include, but need not be limited to, the following main crop plants: corn, soybeans, alfalfa, cotton, sunflower, *Brassica* oil seeds such as *Brassica napus* (eg, canola, rapeseed), *Brassica rapa, B. júncea* (eg mustard (field)) and *Brassica carinata, Arecaceae* sp. (e.g. oil palm, coconut), rice, wheat, sugar beet, cane sugar, corn flakes, rye, barley, millet and sorghum, triticales, flax, nuts, grapes and wine and various fruits and vegetables of various botanical taxa, for example *Rosaceae* sp. (For example, pommel-type fruits such as apples and pears, but also some drupa-type fruits such as apricots, cherries, almonds, plums and peaches, and polyprupa-type fruits such as strawberries, raspberries, red and black currants and gooseberries), *Ribesioidae* sp., *Juglandaceae* sp., *Betulaceae* sp., *Anacardiaceae* sp., *Fagaceae* sp., *Moraceae* sp., *Oleaceae* sp. (for example olive tree), *Actinidaceae* sp., *Lauraceae* sp. (for example avocado, cinnamon, camphor), *Musaceae* sp. (for example trees and banana plantations), *Rubiaceae* sp. (for example coffee), *Theaceae* sp. (eg tea), *Sterculiceae* sp., *Rutaceae* sp. (for example lemons, oranges, tangerines and grapefruits); *Solanaceae* sp. (for example tomatoes, potatoes, pepper, pepper, eggplant, tobacco), *Liliaceae* sp., *Compositae* sp. (eg lettuce, artichokes and chicory-including root chicory, endive or common chicory), *Umbelliferae* sp. (for example carrots, parsley, celery and celery turnip), *Cucurbitaceae* sp. (for example cucumbers-including pickles, pumpkins, watermelons, pilgrim gourds and melons), *Alliaceae* sp. (for example leeks and onions), *Cruciferae* sp. (eg white cabbage, red cabbage, broccoli, cauliflower, Brussels sprouts, pak choi, kohlrabi, radishes, horseradish, watercress and Chinese cabbage), *Leguminosae* sp. (for example peanuts, peas, lentils and beans—for example common beans and large beans), *Chenopodiaceae* sp. (e.g. chard, fodder beet, spinach, beet), *Linaceae* sp. (for example hemp), *Cannabeacea* sp. (for example *Cannabis*), *Malvaceae* sp. (for example ocra, cocoa), Papaveraceae (for example poppy), Asparagaceae (for example asparagus); *Mitragyna speciosa, Nicotinum tobacum, Humulus lupulus*; any produce or smokable herb; useful plants and ornamental plants in the garden and forests including grass, grass, grass and *Stevia rebaudiana*; and the like.

EXAMPLES

Example 1

Analysis of CNV in *Cannabis* Genomes

Male and female *Cannabis* genomes (cultivar 'Jamaican Lion') were sequenced and assembled with their offspring to identify the Y chromosome. These references were further annotated with full-length mRNA (Iso-Seq) sequencing of 5 tissues (female flowers, female seeded flowers, male flowers, female leaves and female roots) and in silico gene model predictions using MAKERS. To confirm the 118 Mb list of putative Y contigs, Illumina's NovaSeq platform to whole genome sequence 40 hemp and drug-type cultivars was used. Using the coverage maps of 9 male genomes, putative Y contigs and male-specific genes were confirmed. These variants were further classified to identify highly damaging mutations in protein coding regions of the genome.

TABLE 1

Results of Iso-Seq Data

| Iso-Seq Annotation | Mother | Father |
|---|---|---|
| Maker Gene models | 27,664 | 32,106 |
| Exome size | 43,651,652 | 53,124,683 |
| CDS size | 34,683,539 | 42,850,812 |
| Exome + Intron (Mb) | 121 | 164 |
| Genome Size (Mb) | 876 | 1,009 |

These whole genome sequence data were utilized to assess copy number variation (CNV) in critical genes in the terpene synthase pathway, cannabinoid synthase pathway and the pathogen response pathway.

Genomes were sequenced with continuous long read mode (CLR). F1 was female. BUSCO: benchmarking universal single-copy orthologs. Software and database versions: BUSCO.py 3.0.2, Augustus 3.3.21, Hmmer 3.2.1, Blast 2.7.1, eudicotyledons_odb10.

TABLE 2

Pacific Biosciences coverage and sequencing statistics of three Jamaican Lion cannabis genomes.

| Coverage | Mother | Father | F1 |
|---|---|---|---|
| N50 | 3,283,100 | 1,668,042 | 3,491,975 |
| Contig number (>5 Kb) | 481 | 1264 | 658 |
| Genome size (bp) | 875,793,298 | 1,009,156,132 | 999,122,115 |
| Complete BUSCOs (%) | 96.1 | 97.0 | 97.3 |
| Single-copy BUSCOs (%) | 83.5 | 63.3 | 63.5 |
| Duplicated BUSCOs (%) | 12.6 | 33.7 | 33.8 |
| Sequencing statistics | | | |
| Unique molecular yield (Gb) | 125 | 150 | 84.8 |
| N50 RL (Kb) | 34.6 | 35.6 | 50 |
| N50 Subread (Kb) | 20 | 24 | 19 |

Male- and female-specific contigs with whole genome alignments from 40 Illumina sequenced cultivars were identified. The parental lines and 6 offspring are included as controls in the Illumina sequenced 40 genomes. Using the default Polar star and Purge haplotig conditions the remaining alternative haplotigs were not included in the CNV analysis.

SNPs and Indels

The DRAGEN unified genotyper was used to map and variant-call the 40 genomes against the maternal assembly. This produced 2M to 12M variants under 50 bp in size. These variants were further annotated with SNPeff to identify 91,440 high impact male and female variants Structural Variation and Gene Models Over 116 Mb of structural variation were observed in the inbred trio with long reads using PBSV (https://github <dot> com/PacificBiosciences/pbsv). In total, 27,664 female genes and 31,108 male genes were identified using 83,464 isoforms identified from the RNA derived from 5 male and female tissue types. Of these transcripts, 98.8% are observed in a recently published *Cannabis* proteome from Orsburn et al. Only 12,026 peptides were found in the mass spectrometry data suggesting low-level transcripts are likely below the sensitivity or sampling obtained with the platform. The distribution of structural variants in *Cannabis* is non-uniform supporting the hypothesis of repeat driven genome plasticity described by Laverty et al. In total, 1,446 genes are partially contained in the structural variation VCF file Copy Number Variation Copy number variation (CNV) in cannabinoid synthase genes has been reported previously. These studies were conducted with fragmented references or assays targeting specific genes. Whole genome analysis (50× coverage) across highly contiguous references has not been completed to date. Illumina sequencing libraries were constructed using PCR (0 and 5 cycles for Jamaican Lion mother and 3 cycles for all other genomes) with unique molecular identifiers (UMIs) for deduplication of over-replicated molecules in the PCR process. This enables more robust copy number analysis with sequence data. A PCR-free Jamaican Lion mother library was also constructed as a control (sample 40). Coverage across 27,644 genes is 99.9% concordant between the PCR and PCR-free control libraries. The most discordant coverage was for JL5 (trio F1) and the 80E samples. These samples all exhibited extreme phenotypes. JL5 exhibited signs of dwarfism, short internodal spacing and stunted growth. The 80E samples have non-serrated leaf structures and powdery mildew resistance.

Example 2

Pathogen Response Genes

*G. chicoracearum* has been shown to cause powdery mildew (PM) in *Cannabis* while *Podosphaera macularis* has been reported to cause PM in *Humulus lupulus* L. (hop) which is a member of Cannabaceae and closely related to *Cannabis*. *Cannabis*-derived powdery mildew can result in significant crop loss while exposing *Cannabis* trimmers to powdery mildew-induced allergies. Many *Cannabis* plants are believed to be powdery mildew-resistant but to date the genetics of this allele have not been described. Identification of this trait can lead to more targeted breeding, increased yields and reduced employee allergen exposure. Cloning and expression of the genes in a non-pathogenic bacterium permits the development of foliar enzymatic sprays against epiphytic pathogens such as PM.

Figure 2:
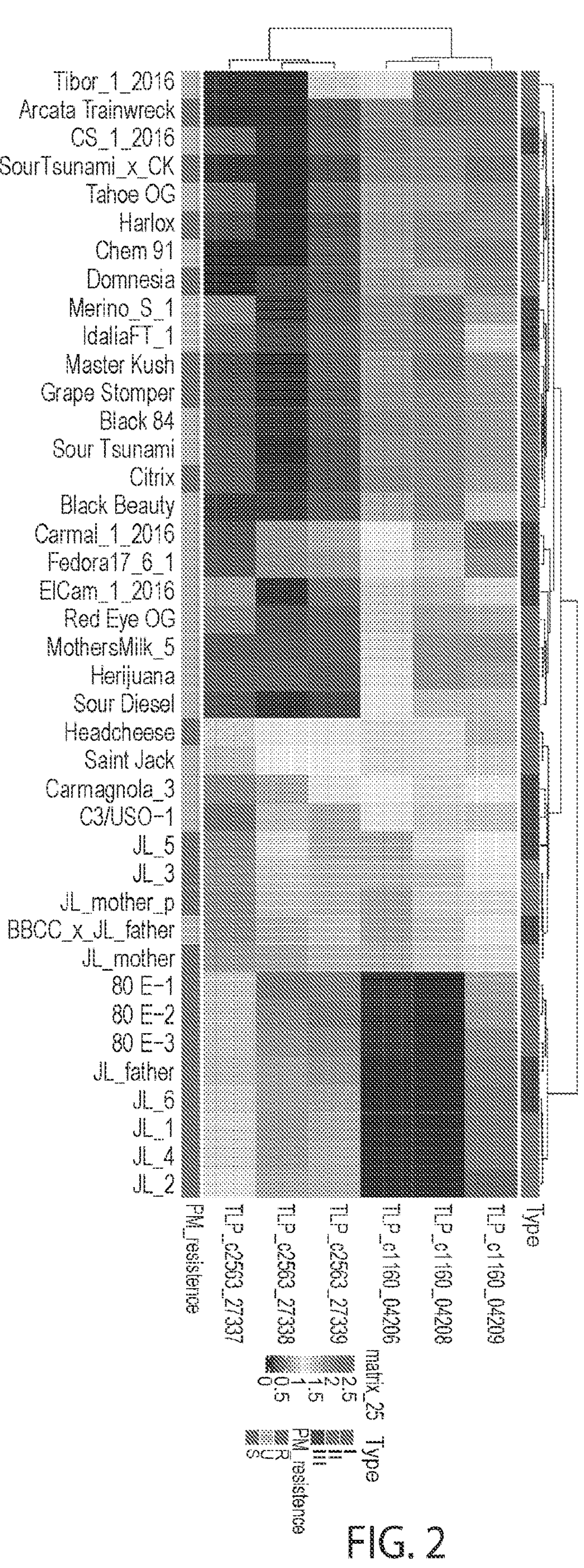
FIG. 2 depicts copy number variation (CNV) of 6 TLPs across 40 cultivars. X-axis contains sample names. Top track contains Type I, II, II status of the samples while the bottom track contains the reported powdery mildew-resistance status. Powdery mildew-susceptible(S) cultivars cluster towards the left (Purple) and have a deletion of CsTLP1. Unknown (U) powdery mildew-resistance status samples are in grey. Along the y-axis, 6 TLPs: deletions are blue in the heat map and amplifications are shown in bright red.
Figure 3:
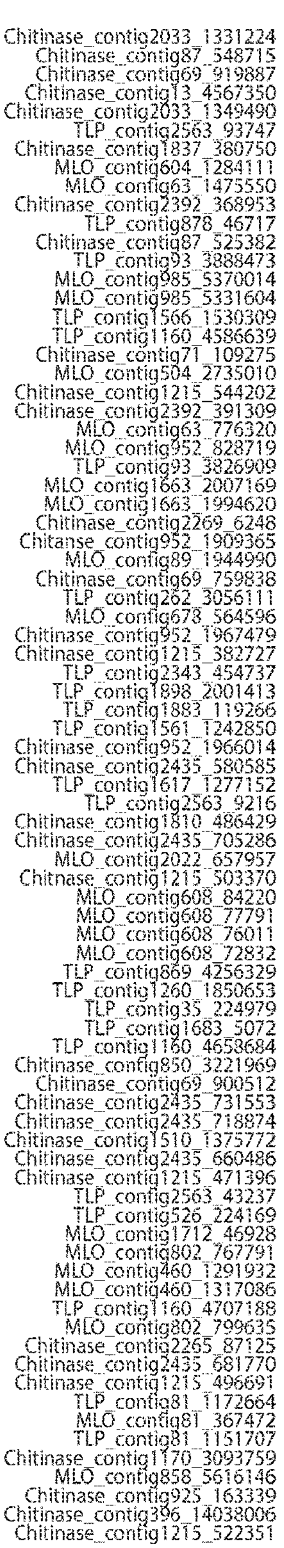
FIG. 3 depicts Iso-Seq expression levels of 82 pathogen response genes. Zero expression detected is shown in blue. Single transcripts detected are shown in pink and the highest expression levels (1000s) are shown in red. Many of the pathogen response genes with significant segregating power in the PCA analysis are also the most heavily expressed genes (chitinase_c2033, chitinase_c13, chitinase_c69, chitinase_c87, and TLP 2563 or 'CsTLP1').
Figure 3:
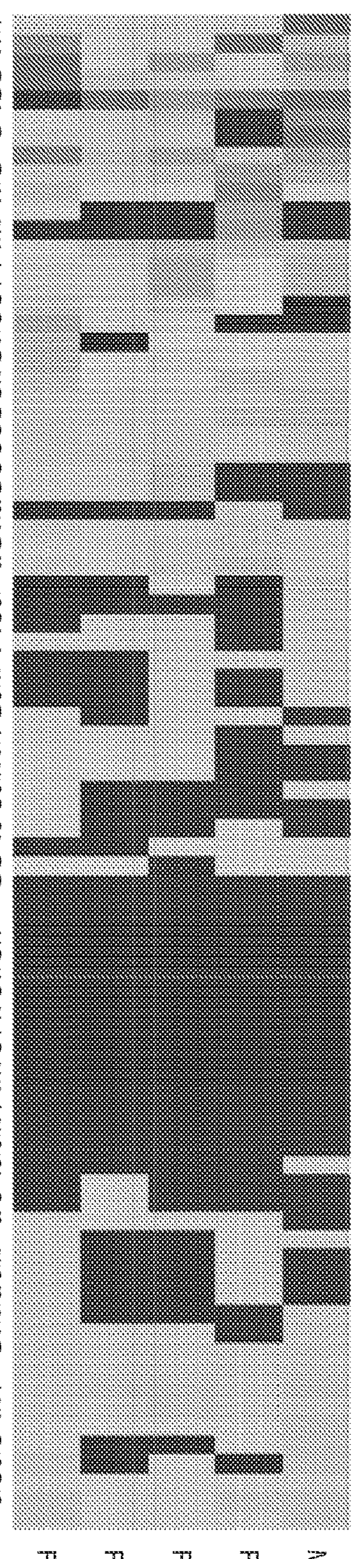
Figure 3:
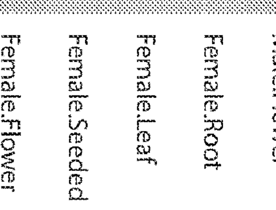
Figure 3:
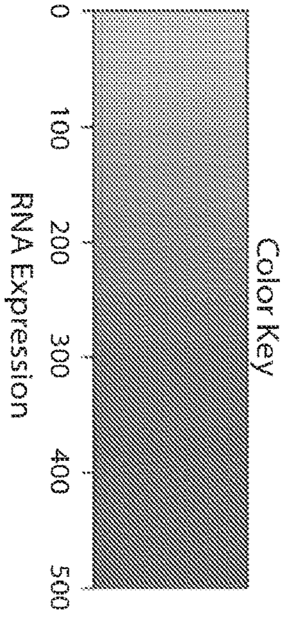

Copy number gains and losses in genes encoding three classes of resistance were evaluated. These data were compared to records from several cultivators on PM resistance of the submitted *Cannabis* DNA samples. The existence of 1 or more copies of thaumatin-like protein (TLP) on contig 2563 was observed in several *Cannabis* cultivars reported to be resistant to PM (FIG. 2). Endochitinase CH25 and lack of mildew resistance loci O (MLO) also correlated with resistance to PM. Several of these genes were heavily expressed in multiple tissues (FIG. 3).

TLPs are responsible for a wide array of pathogen resistance in plants and have been reported to express PM resistance in *Vitis vinifera* (grape) and hops TLPs copy number expansions in spruce are responsible for defense against *Botrytis* and other fungal pathogens. TLP antifungal properties are believed to be due to their β-1,3-glucanase activity. Genetic transformation of wheat with TLP and glucanases results in enhanced resistance to *Fusarium* Jongedijk et al. demonstrated synergistic activity of chitinases and β-1,3 glucanases in transgenic tomato. The invention relates to detection of endochitinases, MLO and other PR genes which can augment or attenuate the response.

Twenty-three TLPs, 35 chitinases, and 24 MLO genes were found in the Jamaican Lion reference genome and were evaluated for gene expression in 5 parental tissues and genomic copy number variation across 40 genomes. Many PM-susceptible cultivars reveal deletions of a TLP gene we have termed "CsTLP1" while PM-resistant cultivars contain CsTLP1 or copy number gains in CsTLP1. RNA expression of CsTLP1 was observed in all tissues except roots, with the highest expression in male flowers and female leaves. Due to the limited number of samples in the dataset and the presence of the Jamaican Lion family potentially producing synthetic associations, cloning and expression of putative resistance genes is required.

Figure 4:
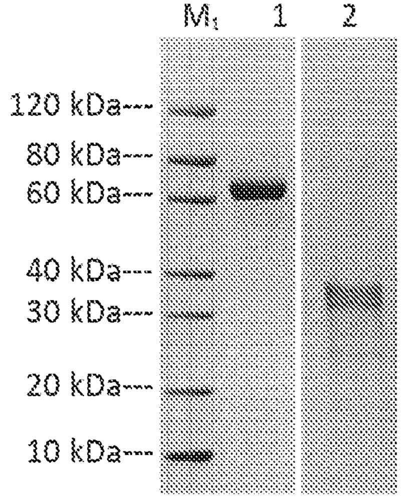
FIG. 4 depicts experimental data: A) SDS-PAGE and B) Western blot analysis of CsTLP1 expression in *E. coli*. Lane M1: Protein marker (GenScript, Cat. No. M00516); Lane 1: Bovine serum albumin (2.00 μg); Lane 2: CsTLP1_2563 (reducing condition, 2.00 μg); Lane M2: Protein marker (GenScript, Cat. No. M00521); Lane 3: CsTLP1_2563 (reducing condition); primary antibody: mouse-anti-His mAb (GenScript, Cat. No. A00186).
Figure 4:
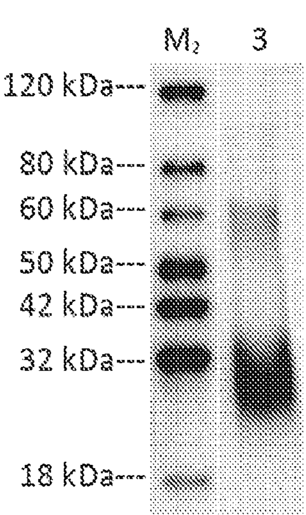
Figure 5:
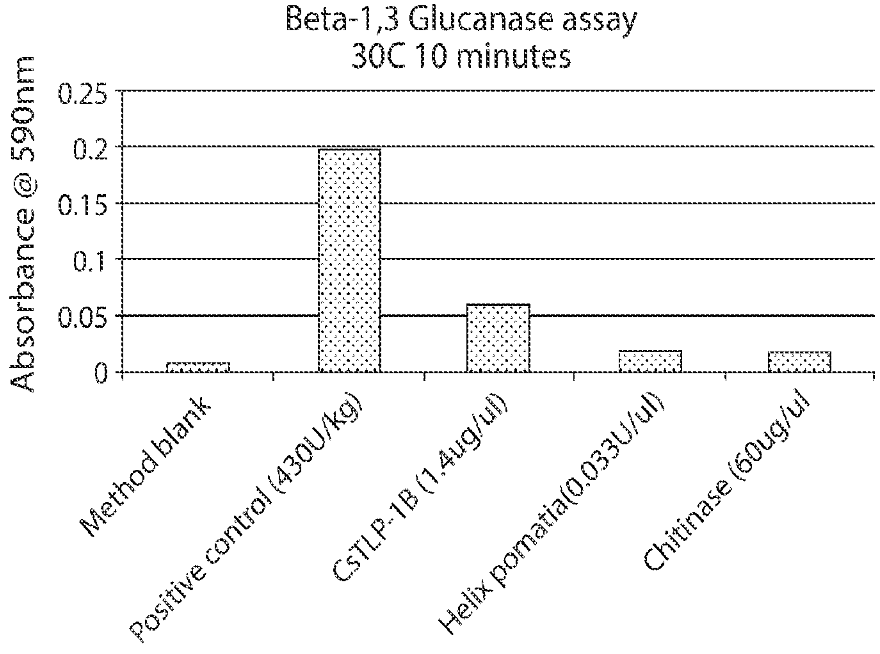
FIG. 5 depicts a β-glucanase assay (Megazyme) that demonstrates activity of the expressed CsTLP1 protein is lower from the inclusion bodies (CsTLP1-IB) fraction than from the cell lysate. Dialysis of the protein increases CsTLP1 activity implying high-salt buffers may inhibit enzyme activity. Activity is compared to a *Helix pomatia* β-glucanase (Sigma) and a *Trichoderma viride* chitinase (Sigma). The positive control was provided in concentrated form by Megazyme. *H. pomatia* β-glucanase was isolated from a snail stomach with optimal activity at 50 to 55° C. CsTLP1 has lower activity at 30° C. Method blank contained the substrate and positive control enzyme but was precipitated with no incubation time.
Figure 5:
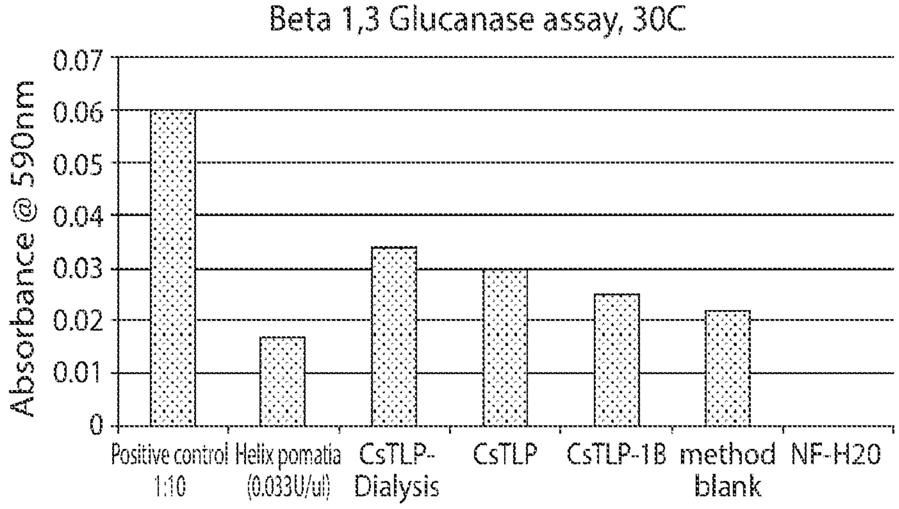
Figure 6:
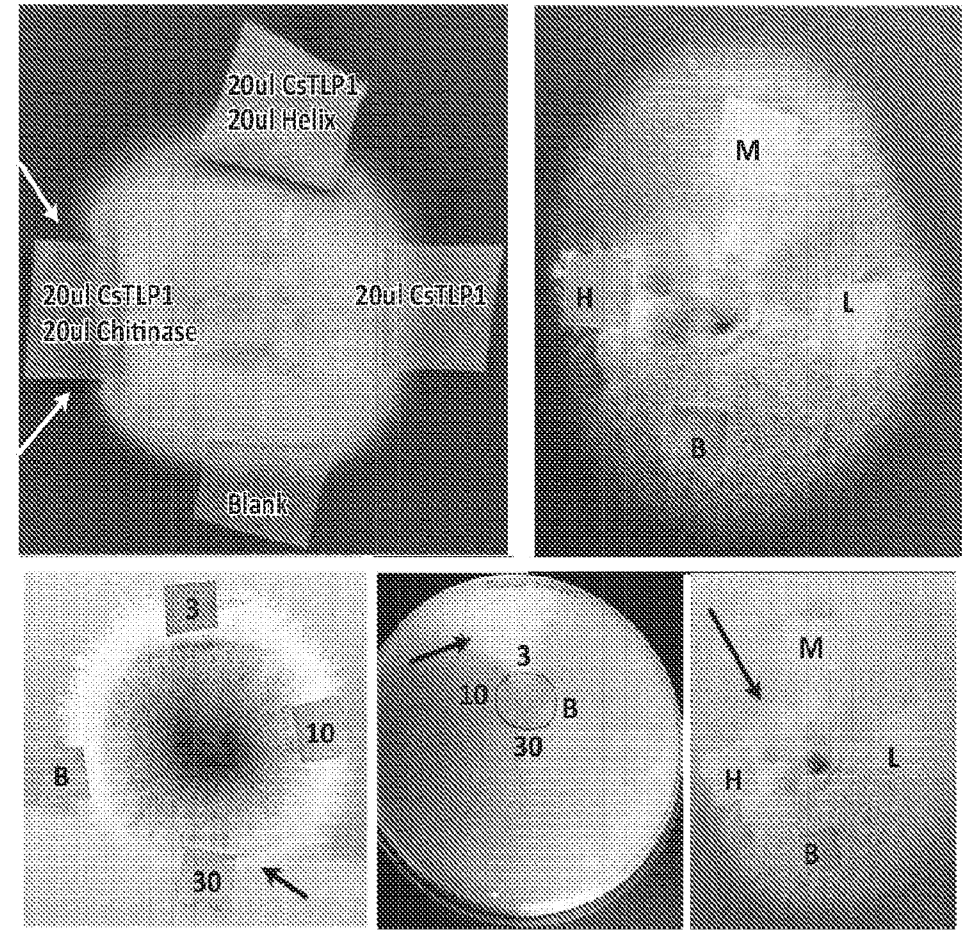
FIG. 6 depicts Upper Left) *Penicillium chrysogenum* grown in the presence of dialysis CsTLP1, *Trichoderma viride* chitinase (Sigma) and a *Helix pomatia* β-1,3 glucanase. Upper Right) Enlarged image of *Fusarium* and CsTLP1 (3 μg, 10 μg, 30 μg, and Blank)+*T. viride* chitinase (40 μL, 20 μL, 10 μL applied at 600 μg μL−1) plated on potato dextrose agar. Lower left) CsTLP applied only to *Fusarium* (3 μg, 10 μg, 30 μg, and Blank). Lower middle) Same colony as shown in lower left, two weeks later. In this case the 3 μg addition of CsTLP demonstrated reduced pigment (aurofusarin) expression. Lower right) Same image as upper right with different contrast to emphasize aurofusarin expression. Fungal cultures were incubated for 3 days to allow for development of a sizable colony and then assessed for disturbed growth after application of protein (CsTLP or controls) on Whatman paper. Images were collected before and after the CsTLP1 protein was applied and grown for another 36 hours. Subsequent to this, similar dosages of *T. viride* chitinase (3 μg, 10 μg, 30 μg, Blank; Sigma) were placed on the Whatman paper to identify synergistic effects. (L=Low, M=Medium, H=High)
Figure 7:
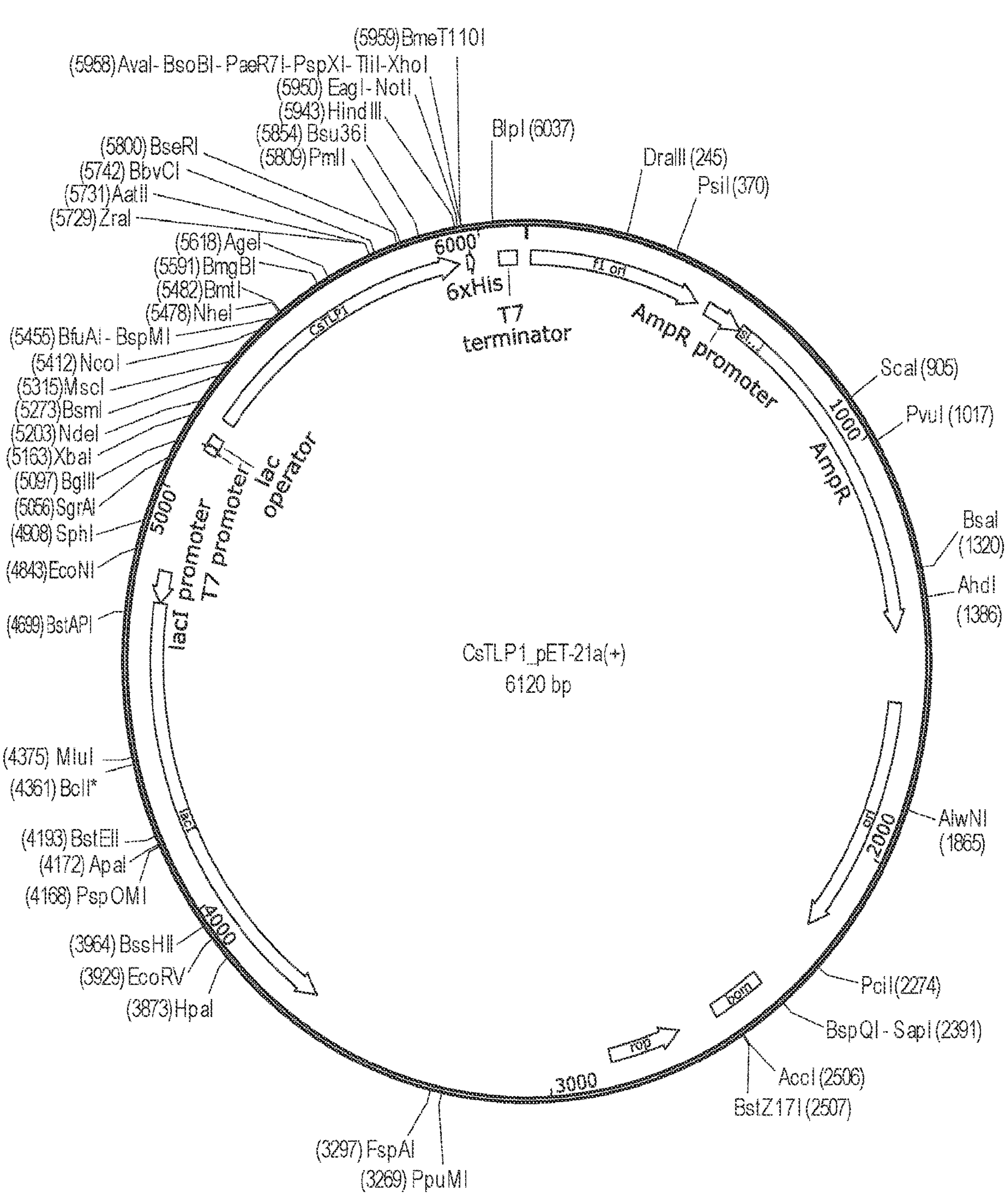
FIG. 7 depicts cloning and expression of CsTLP1_2563 into pET30a (+) which was outsourced to Genescript. 6× Histag was added to the peptide and the 20 amino acid N-terminal membrane signal peptide was removed for expression in *E. coli*. Other TLP targets can be used: In addition to the 3 TLP genes on contig2563, 20 other TLP genes exist in *Cannabis*.

CsTLP1 was cloned into a pET-30a vector for expression in *Escherichia coli* for in-vitro fungicidal assays. Of the expressed and purified CsTLP1 protein, 75% of the expressed protein was found in the inclusion bodies. *G. chicoracerum* is an obligate biotroph and is difficult to culture for controlled fungicidal evaluation of CsTLP1. Instead, purified CsTLP1 was applied to cultures of *Aspergillus flavus, Penicillium chrysogenum* and *Fusarium oxysporum*, which are other fungal pathogens of *Cannabis*. Growth of *A. flavus* and *P. chrysogenum* was not inhibited by CsTLP1 but growth of *Fusarium oxysposum* was inhibited (FIGS. 4, 5, 6). Co-application of CsTLP1 and *T. viride* chitinase inhibited both *P. chrysogenum* and *F. oxysporum* growth in vitro. β-1,3 glucanase assays were utilized to confirm activity of the expressed CsTLP1 protein.

Example 3

Cannabinoid Synthase Genes

Thirty-nine cannabinoid synthase genes were evaluated for CNV across 40 genomes. Using the coverage maps across THCA synthase (THCAS), cannabidiolic acid synthase (CBDAS) and cannabichromenic acid synthase (CBCAS) (contigs 741, 1772, 756), plant primary cannabinoid expression was classified into Type I, II, and III plants. These common deletions reflect the Bt: Bd allele suggested by de Meijer et al. Plants lacking a functional CBDAS gene are Type I plants. Type II plants have both functional genes and synthesize both THCA and CBDA. Plants with no functional THCAS gene and a functional CBDAS gene are Type III plants. Plants lacking both functional genes are Type IV plants and only synthesize the precursor cannabigerolic acid (CBGA). While deletions of entire THCAS and CBDAS genes are the most common Bt: Bd alleles observed, it is possible to have plants with these genes where functional expression of the enzyme is disrupted by deactivating point mutations.

Of interest is the frequent deletion of the CBCAS gene cassette (~2 Mb) seen on contig 756. This contig contains 8 CBCAS genes directionally orientated and over 99.4% identical to each other. One CBCAS gene has recently been cloned and expressed by Laverty et al. and was previously known as "Inactive THCAS". Winnicki et al. demonstrated that multiple cannabinoids can be expressed from a single cloned synthase gene by modulating the yeast growth conditions (U.S. Pat. No. 9,526,715 & 9,394,510). Hemp lines have also been more difficult to grow while maintaining a THCA concentration below the 0.3% THCA limit mandated in many jurisdictions. In particular, the THCA levels appear to increase in varieties from equatorial climates. Thus, it is possible that the presence of this cassette or other cannabinoid synthase CNVs are responsible for low levels of promiscuous THCA expression in some plants lacking a THCAS gene (Type III plants).

This CBCA deletion also harbors an expressed gibberellin transporter (NPF3) known to be involved in pathogen response. Other pathogen response genes also contained in this CBCAS deletion are RMT1 (involved in viral defense), PIP1 (PAMP-induced secreted peptides), and NIP1 (aquaporin involved in $H_2O2$ pathogen response). This implies that optimization of cannabinoid expression may need to be carefully monitored for pathogen susceptibility. Cannabinoid synthase CNV maps may play an important role in breeding for compliant pathogen-free hemp cultivars that do not synthesize residual THCA.

Example 4

Y Chromosome Genes

To identify the Y chromosome, 40 genomes were aligned to the paternal Pacific Biosciences reference assembly. Nine male genomes, 2 monoecious genomes and 29 female genome alignments highlight contigs that are covered exclusively in male plants while having half of the coverage over other contigs in female genomes. These contigs with double coverage in females are believed to be the X chromosome while contigs with zero coverage in females are labeled as Y contigs.

To confirm this, Iso-Seq mRNA reads expressed in male flowers were mapped to the female reference. The 'female-unmapped' male mRNA reads were then mapped to the male reference to find male-specific mRNA expression with no homology to the female reference. These male-specific mRNAs were then intersected with the male-specific contigs to identify 574 genes on the non-recombining region of the Y chromosome. Prentout et al. has reported a similar approach using Illumina based RNAseq with Type I *Cannabis* plants but the data is not currently available (Prentout 2019). It is important to note that reads that do not map to the female reference can be either 1) the Y chromosome or 2) a structural variation in the female reference genome. Only CNVs that exist in all males and females are considered for X and Y categorization. Genes of interest on the Y chromosome include Enhanced Downey 2, FT Flowering Locus T, Flowering Time control protein FY, PIN2 (Auxin efflux carrier component 2), AP2-like ethylene-responsive transcription factor CRL5, and Protein trichome birefringence-like 6.

Example 5

RNA Expression

Iso-Seq data was collected mainly to annotate the genome. The RNA sequencing libraries do not appear to be saturated suggesting limited dynamic range in the transcript counts. There are no biological replicates to utilize for statistical analysis. The RNA was harvested from only parental tissues. The transcript counts for TLPs, chitinases, and MLOs are presented (FIG. 3) demonstrating the highest transcript counts for CsTLP1, chitinase_c2033, chitinase_c13, chitinase_c69 and chitinase_c87.

Example 6

Anti-Fungal Activity

CsTLP1 was first confirmed to have β-1,3 glucanase activity using a malt β-glucanase assay (Megazyme). This was complimented with anti-fungal assays described by Misra et al. Of interest is the visible reduction in red pigmentation of *Fusarium oxysporum* colonies. Red pigmentation in *F. oxysporum* has been reported to be the product of aurofusarin expression. Vujanovic et al. (Vujanovic 2017) describe a reduction in *Fusarium* aurofusarin expression with mycoparasitic and chemical control agents supporting the antifungal properties of CsTLPs and chitinases.

CsTLP Expression

A 225 amino acid (MW=23,714.5) peptide (CsTLP) was expressed in *E. coli* DH10B in 1 L of terrific broth (TB, 24 g $L^{-1}$ yeast extract; 20 g $L^{-1}$ tryptone; 4 mL $L^{-1}$ glycerol; 0.017 M $KH_2PO_4$, 0.072 M $K_2HPO_4$) with a 6× Histag. A 20 amino acid N-terminus signal peptide was removed.

The amino acid sequence was:

```
                                          (SEQ ID NO. 1)
MIQNNCGRTTWPATQSGSGSSQLSTTGFELASGASQSIEIPAGPWSGRF

WGRDGCSTDSSGRFACASGDCASGTVECNGAGGVPPTTLVEITVAENGG

QDFYDVSNVDGFNLPVSVRPEGGNGDCQESTCPNNLNDGCPADLQYKSG

DDVVGCLSSCAKYNMDQDCCRGAYDSPDTCTPSESANYFEQQCPQAYSY

AYDDKTSTFTCSGGPNYLITFCPHHHHHH.
```

CsTLP1 was eluted in 20 Mm Tris, 500 mM NaCl, 10 mM reduced glutathione (GSH), 1 mM glutathione disulfide (GSSG), 20% glycerol, pH 7.5.

β-1,3-Glucanase Assay.

A malt β-D-glucanase assay (Megazyme) was used to measure CsTLP1 enzyme activity according to the manufacturer protocol. The protocol was scaled down to fit in 1.5 mL Eppendorf tubes. One hundred and fifty μL of dye-labeled azo-barley glucan was mixed with 150 μL of enzyme and incubated at 30° C. for 10 minutes. Nine hundred μL of precipitation solution A was used to precipitate undigested glucan. Samples were centrifuged for 10 minutes at 1000×g to pellet digested glucan. Dye-labeled digested glucan remained in the supernatant and absorbance was measured at 590 nm.

Example 7

Data are available at NCBI under Project ID PRJNA575581 and SUB6635057.

Example 8

TLP Genes in *Cannabis*

There are 23-24 TLPs in *Cannabis* genomes surveyed to date. To prioritize candidate TLP genes, tissue specific gene expression was compared to protein expression. Target TLPs were prioritized based on high male and female leaf expression and protein expression. The copy number variation observed on contig2563 demonstrates the highest mRNA expression in Jamaican Lion.

Jamaican Lion is believed to be PM resistant. To confirm this, powdery mildew was inoculated under high humidity. These exposures failed to produce colonies however this is not a thorough test of resistance (Punja 2018). Sequence coverage over the 23 CsTLP genes across 40 whole genome shotguns clusters Jamaican Lion closest to 80-E samples.

The most thorough test of resistance requires full life cycle exposure to powdery mildew and minimal signs of colonization. Sample 80E exhibits this full life cycle exposure and resistance. Given the diversity of TLP genes in *Cannabis* it is unlikely pathogen resistance is a binary trait. *Humulus lupulus* has several loci responsible for varying degrees of resistance in hops (Wolfenbarger et al. 2014; Gent et al. 2015; Twomey et al. 2015; Wolfenbarger et al. 2016; Gent et al. 2017; Gent et al. 2018). Quantitative assays of both gene copy number and RNA are critical to understand the variable penetrance of this trait.

Quantitative RT-PCR primers were designed to target both DNA and RNA of Contig2563, Contig93, Contig81, Genomic_Control/IspE (Autosomal control). The DNA copy number and the RNA copy number can be compared to another autosomal target in the cannabinoid synthase pathway. The relative change in gene copy number and expression is used to calculate a PM resistance score.

An additional qPCR assay was designed to detect the presence of Golovinomyces chicoracearum (Powdery mildew most commonly found on *Cannabis*). An ideal outcome would demonstrate presence of high DNA copy number and RNA expression of Contig2563 and no detectable signal from Golovinomyces chicoracearum.

Example 9

Lysis of Fungi

Various enzymes for lysis of fungi were compared to more traditional LiDS lysis methods.

Figure 9:
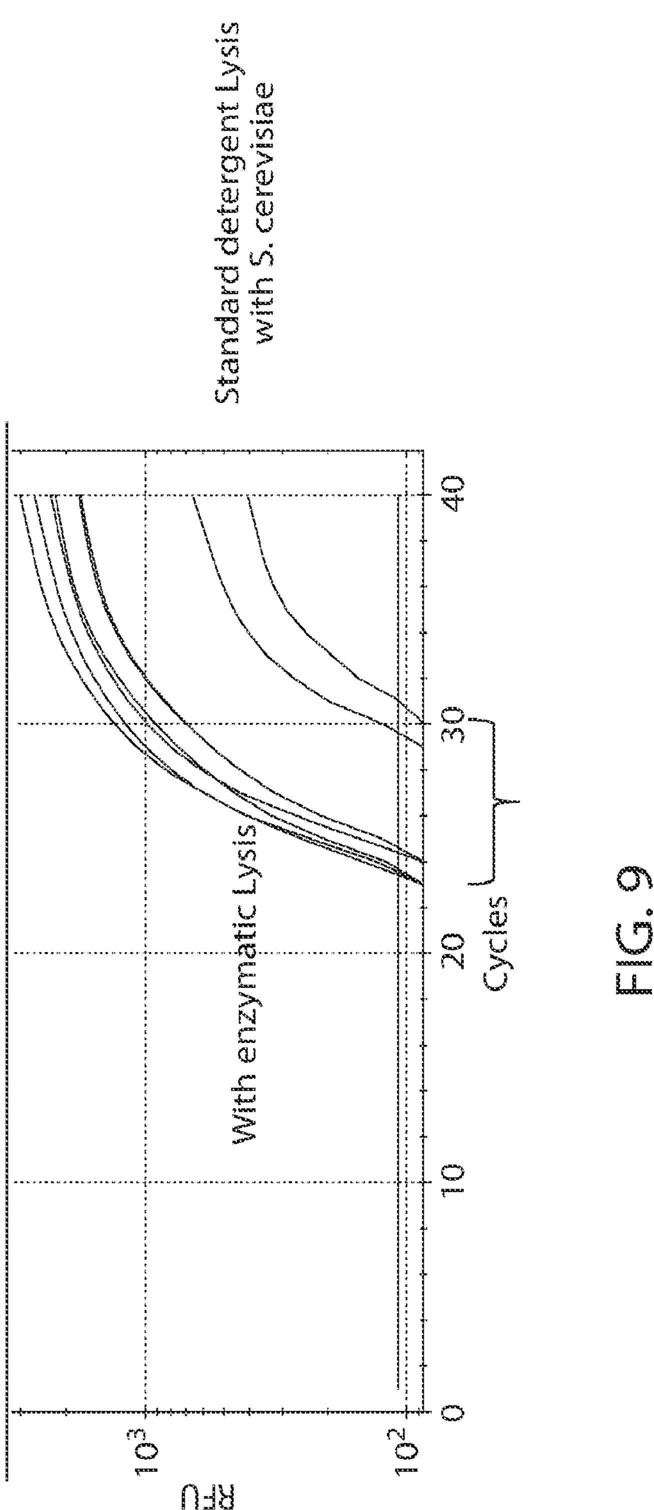
FIG. 9 depicts qPCR results of experiments comparing lysis compositions and methods of the invention with traditional methods.

*S. cerevisiae* (Microbiologics part number 0699L derived from ATCC #97633) was grown 18 hours in 200 ml TSB. 2 ml was pelleted and resuspended in 250 ul ddH20 and treated with 50 ul of (40 ug) CsTLP1 and 50 ul (20 ug) CsChitinase at 37 C for 30 minutes. After this enzymatic digestion was complete, 2% LiDs was added and DNA purified using 300 ul of magnetic beads (Medicinal Genomics part #420001 SenSATIVAx). After magnetic separation for 10 minutes, 3×70% ethanol washes (300 ul) were performed. Beads were dried at Room Temperature for 10 minutes and eluted in 50 ul of ddH20. 5 ul of DNA was utilized in qPCR of 18S rDNA target. This qPCR result was compared to a control purification that omitted the enzymatic lysis step. (FIG. 9)

This demonstrates a 6-8CT shift in detection of 18S DNA in *S. cerevisiae* utilizing enzymatic digestion compared to using just detergent lysis alone. This equates to 64 to 256 fold improvement in lysis and DNA recovery. This surprising result can greatly aid in the sensitivity to detect certain fungal species on *Cannabis*. Not all fungi may respond as favorably. This will depend on the life cycle of the fungi and the thickness of their glucan and chitin cell walls and may be very species specific and life cycle specific.

Example 10

PCR Conditions

Amplification was performed using 2 ul of DNA/RNA from a 100 ul boil prep (Medicinal Genomics-Leaf Punch Lysis Solution) of 4 mm hole punch in a *Cannabis* leaf. Brilliant III UltraFast qPCR enzyme was utilized for qPCR (Agilent) scanning in FAM, HEX, Texas Red, CY5 (Agilent Aria).

- 10 ul of Brilliant III Master Mix
- 0.5 ul CsTLP1 Primer-Probe mix (12.5 μM primer, 6.25 μM probe)
- 0.5 ul Genomic_Control Primer-Probe mix (12.5 μM primer, 6.25 μM probe)
- 0.5 ul CsTLP4 Primer-Probe mix (12.5 μM primer, 6.25 μM probe)
- 0.5 ul CsTLP2 Primer-Probe mix (12.5 μM primer, 6.25 μM probe)
- 0.2 ul DTT 100 μM
- 1 ul RT/Block
- 4.8 ul ddH20
- 2 ul DNA
- 20 ul Total Cycling Conditions 1) 50C 10 minutes
2) 95C 3 minutes
3) 95C 5 seconds
4) 65C 30 seconds
5) Goto step 3 39 times.

The various methods and techniques described above provide a number of ways to carry out the application. Of course, it is to be understood that not necessarily all objectives or advantages described are achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by including one, another, or several other features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, any numbers expressing quantities of ingredients, properties such as molecular weight, reaction conditions, and so forth, used to describe and claim certain embodiments of the disclosure are to be understood as being modified in some instances by the term "about." Accordingly, in some embodiments, the numerical parameters set forth in the written description and any included claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are usually reported as precisely as practicable.

In some embodiments, the terms "a" and "an" and "the" and similar references used in the context of describing a particular embodiment of the application (especially in the context of certain claims) are construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Variations on preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Sequences are provided. N-Terminal and C-Terminal versions of the proteins can be used. An example of a N-Terminal 6×HisTag of CsTLP1.

Comment: > CsTLP1 N-terminal His Tag (SEQ ID NO. 2)

MHHHHHHIQNNCGRTIWPATQSGSGSSQLSTTGFELASGASQSIEIPAGPWSGRF

WGRDGCSTDSSGRFACASGDCASGTVECNGAGGVPPTTLVEITVAENGGQDFY

DVSNVDGFNLPVSVRPEG

GNGDCQESTCPNNLNDGCPADLQYKSGDDVVGCLSSCAKYNMDQDCCRGAY

DSPDTCTPSESANYFEQQCPQAYSYAYDDKTSTFTCSGGPNYLITFCP*

CsTLP1

>*Cannabis sativa* Jamaican Lion (v02-2019, unmasked: draft assembly), Name: EFW9900027339-RA, Type: CDS, Feature Location: (Chr: contig2563, complement(join(94046..94725, 100013..100070))) Genomic Location: 94046-100070

(SEQ ID NO. 3)

ATGAAGATTCAAATAATACTCTTCTTTACTGTCGCCCTAGCTTTAATCTTTGC

TGCAGGGACGAATGCAGCTACCGTCAACATTCAAAACAACTGCGGA

AGAACCATCTGGCCAGCAACCCAATCCGGCAGCGGAAGTTCACAACTCTCA

ACCACTGGTTTCGAGTTAGCATCAGGAGCCAGCCAGTCCATCGAAATC

CCAGCCGGACCATGGTCGGGGCGCTTCTGGGGTCGAGATGGTTGCTCCACT

GACTCATCCGGCAGGTTCGCGTGCGCTAGCGGAGACTGTGCCTCTGGT

ACGGTGGAGTGTAATGGTGCAGGCGGAGTCCCTCCAACAACTCTGGTCGAA

ATAACCGTTGCAGAAAACGGTGGACAAGATTTCTACGACGTGAGCAAC

GTGGACGGGTTCAACTTACCGGTTTCGGTTAGGCCAGAAGGTGGTAATGGG

-continued

GATTGCCAGGAGTCAACGTGCCCAAACAACCTAAACGACGGTTGCCCA

GCTGATCTACAGTACAAATCCGGAGACGACGTCGTTGGGTGCCTCAGCTCTT

GCGCCAAGTATAATATGGACCAAGACTGTTGTAGAGGAGCTTATGAT

TCTCCAGACACGTGTACTCCTAGTGAGTCCGCTAACTACTTCGAGCAACAAT

GCCCTCAGGCTTACAGCTATGCTTATGATGATAAGACCAGCACTTTT

ACTTGCTCCGGTGGACCTAACTATCTTATCACTTTCTGCCCATGA

CsTLP2_93_3888473
>*Cannabis sativa* Jamaican Lion (v02-2019, unmasked: draft assembly), Name: EFW9900006817-RA, Type: CDS, Feature Location: (Chr: contig93, join(3888925..3888994, 3889084..3889753, 3890323..3890608)) Genomic Location: 3888925-3890608

(SEQ ID NO. 4)

ATGGATCCTTATTCAAGGTTCTCATTTTCACTCATTCTCAGCTTTGTCGTCCT

ACTTCTCACCTCCAGAGGCGTCACAGCTGCCACCTTTAACTTCGTT

AATCGATGTGACTACACTGTTTGGCCGGGCATTCTAGCTAATGCCGGAAGCC

CAAGACTCGACAGCACAGGATTCGAGCTACCAAAGGACACCTCTCGA

TCTTTCCTGGCTCCGACGGGTTGGTCGGGTCGTTTTTGGGGTCGGACGGGTT

GTACTTTTGATGAATCAGGATCCGGGTCCTGTCTCACCGGAGACTGT

GGTTCTGGCGTGGTCGAGTGCAACGGCGCCGGAGCTGCACCGCCAGCGACC

CTCGCCGAGTTCACTTTAGGAACCGGCGGGCAGGACTTCTACGACGTC

AGCCTCGTCGACGGCTATAACTTGCCCATGGTCGTTGAAGGAACTGGCGGG

TCGGGCCTGTGCGCCTCCACGGGTTGCCCCACCGACTTGAACCAGCAA

TGCCCGTCGGAGTTGAGGGTCGGGAACGGTAACGCGTGTAAGAGCGCGTGC

GAGGCTTTCGGGACCCCAGAATACTGTTGCAGCGGCGCGTATGGTACA

CCCGCCACTTGTAGGCCGTCAGTTTACTCTGAGATGTTTAAGTCCGCGTGTC

CCAGATCGTATAGCTACGCCTACGATGATGCCACCAGTACGTTTACG

TGTACGGGAGCTGATTATACGGTGACGTTTTGTCCATCTTCACCAAGCCAAA

AATCCACAAGAGATACTACGCCAACAGCAGCAGGGTCACAATCCGGG

GCAACGTATTCGGATCCAGGACAACAACAGCAACAACCCGAGGTAACATAT

CCAGAAGCAGGATCCGGGTCGGGTACTGGAAGTGGATCCGGAGGAACC

CTTTTAGCAGATGGGACATGGTTGGCTGGTTTGGCAATGGGAGACTCACCA

AGAACAGTCTTATCACCCTCAACTCTACGTGTTGCACTCATAGCCTTT

GTAGCTTTTTATTCCATCTTATTAAGAAAGTTGTAA

CsTLP3_93_38226909
>*Cannabis sativa* Jamaican Lion (v02-2019, unmasked: draft assembly), Name: EFW9900006815-RA, Type: CDS, Feature Location: (Chr: contig93, join(3827120..3827180, 3827260..3827953, 3828922..3829117)) Genomic Location: 3827120-3829117

(SEQ ID NO. 5)

ATGGATCGGATCATTCTTACCGGGTCACTTCTCACACTCCTCACTTTCTCTTT

CGTCTTAGAAATAGAGTCAACGTCGTTCAAATTAGTAAACAAATGC

AGGAACACCATATGGCCCGGCTTGTTATCCGGTGCCAACTCAGCTCCGCTCC

CCACCACCGGCTTCGTTCTCCACAGCGGCGAATCCCGGACCTTACGC

ATACCCAGAGCGTGGTCGGGTCGTCTATGGGCTCGGACCCATTGCGGCCAC

GACTCAACCGGGAAATTCACTTGCATCGCCGGGGACTGCGGCTCAGGC

AAGCTGGAGTGTGAAGGAGCCGGGGCCAAGCCGCCAGCTACACTAGCTGAG

TTCACTCTTAACGGCGCAGACGGCTTGGACTTCTACGACGTCAGCTTA

GTCGACGGGTACAACATCCCGATGTTGATCGTCCCCAAGGGAGGTACAAGA

GGTGGATGCGGCGCCACCGGTTGTCTCGTCGACTTAAACGGGGCTTGT

CCGACCGCGTTGCGAGTGGCGCGTGCTAATGGCAAAGGGAGCGTAGCGTGT

AGGAGCGCGTGTGAAGCGTTCGGGGATCCCCGCTTCTGTTGTAGTGAG

GCGTACTCTACACCTGACACGTGTGGACCTTCTCCTTATTCGCTCTACTTCAA

ACACGCTTGCCCACGCTCGTATAGCTACGCGTACGATGACAAAACC

AGCACTTACACGTGCGCCTCCGCTGATTATACTATTATATTTTGCCCATTACC

CTATACGAGCCAGAAAGTGTTGGGAGCAAGAAAAGATGGGATACCA

CTACCACTGGTGAATAAGACCATGATGTACTTAAGAAGCCGACACTCAAGC

GGAGCTGCAGCATCGTCCACAGGTCTTTCTTCTTTGCTATTTATGGCC

CTTGCAGCCACTAATGCACTGCCACTTTTGCTATCATGGCCAATTTATAACT

CTTTGTGA

CsTLP81_81_1172664
>*Cannabis sativa* Jamaican Lion (v02-2019, unmasked: draft assembly), Name: EFW9900012315-RA, Type: CDS, Feature Location: (Chr: contig81, complement join(1172980..1173109, 1174021..1174720, 1174811..1174874))) Genomic Location: 1172980-1174874

(SEQ ID NO. 6)

ATGGCTTCTCTTCATCAATTTCTCCTCTTCTCTCTAATCATTCCCTTCTTCCAT

TTCCTTCAAGGTGTTAATTCAGCTACATTCACAATCACAAACGAA

TGCAGTTACACAATTTGGCCGGGAATTTTATCCGGTGCCGGAACTTCACCAC

TTTCCACCACTGGATTTTCTCTCCAACCGGGAGAATCAAACTCTCTC

CAAGTACCAATTTCTTGGTCAGGTCGATTATGGGGTCGAACCCTTTGCTCCA

CAGACCCAACAACATCCAAATTCTCCTGCGTCACAGGCGATTGTGGC

TCCTCCACCGTTGAATGCAGCGGTGCCGGAGCTATTCCTCCGGCGACTCTAG

CTGAATTCACACTTAACGGCGCTGGAGGATTGGATTTCTACGATGTT

AGCCTTGTTGACGGTTATAACCTCCCCATGAAGGTTGCTCCGGTGGTCGGTG

AAGGTACCGGCGGGAACTGTACTACGACGGGTTGTTTGGTGGATTTG

AATCCAGGGTGTCCGGCGGAATTGAAGGTTTCGTCGGCGAGTGTGGAGAGC

GTGGCGTGTAAAAGCGCGTGTGAGGCTTTTGGGGACCCACAGTTTTGT

TGTAGTGGGGCCTACGCTACTCCTGACACGTGTAAACCTAGCTCTTATTCTC

TATTCTTTAAAAATGCGTGTCCAAAAGCTTATAGCTACGCTTATGAC

GATGGAACCAGTACCTTCACATGTGCCAACGCCAATTACGTAATTACCTTTT

GCCCTTCGCCAACTACAAGTGTAAAGTCTTCTAACGGGAAGTATCCC

GAGGCAGCCGAAGTATCGGCCAGTTCTCGCAAAACGACACCGTATCTCATT

GGATTTGGCGTTTTAGGGGCAAGTTGGGGATTTCGGCAACTATTCATT

TAA

>Chitinase_c69_900512
*Cannabis sativa* Jamaican Lion (v02-2019, unmasked: draft assembly), Name: EFW9900022330-RA, EFW9900022330, augustus_masked-contig69-processed-gene-3.17-mRNA-1, Type: mRNA, Feature Location: (Chr: contig69, complement(join(900512..900690, 901415..901790))) Genomic Location: 900512-901790

(SEQ ID NO. 7)

ATGACGGTTATTTGTAGTAACGCTGGATACTGTGGCCAGACAGATGCCTATT

GTGCCCCTGAAAACTGCCAAAGCCAATGTCGAACCCCATCTCCCCCA

-continued

CCACCACCGTCACCGCCACCTCCTCCCTTCACGCCACCACCTCCGATTTCTCC

CGATGATGATAGTCACATCATTACTTCCTCACTTTTCGAGGAGATG

CTTACCTATCGAAATGATCATCGATGCAAAAGTAATGGCTTCTACACTTACG

ACGCCTTCATAACTGCTGCTAGAATTTTTCCGGGCTTTGATACTACT

GGCTCTCTTGAAACTCGTACAAGAGAACTAGCTGCGTTCTTTGGCCAAACTT

CTCAGGAAACCACAGGAATACATACTGGTTTGGAGTGCGGCCACGGT

GTTGATGACCGGGTCATAGATAGGATTGGCTTCTATGAAAGGTACTGCCTTA

TACTAGGAGTAAGCACTGGGGACAATTTGGACTGTTACAATCAACGT

CCTTTCAATGATGATCCACAAACATCTTATGGAGTCCTCAAAATGTCTGTTC

AAGAATAG

>Chitinase C69_900512
Genomic Location: 900512-901790, EFW9900022330
Subclone into *E.coli* Expression Vector pET30a using Nde I and Hind III
(SEQ ID NO. 8)

MHHHHHHTVICSNAGYCGQTDAYCAPENCQSQCRTPSPPPPPSPPPPPFTPPPPIS

PDDDSHIITS

SLFEEMLTYRNDHRCKSNGFYTYDAFITAARIFPGFDTTGSLETRTRELAAFFGQ

TSQET

TGIHTGLECGHGVDDRVIDRIGFYERYCLILGVSTGDNLDCYNQRPFNDDPQTS

YGVLKM

SVQE*

>Chitinase C69_900512
*Cannabis sativa* Jamaican Lion (v02-2019, unmasked: draft assembly), Name: EFW9900022332-RA, Type: CDS, Feature Location: (Chr: contig69, complement(join(920595..920752, 920949..921423))) Genomic Location: 920595-921423
(SEQ ID NO. 9)

ATGAAATACTCTTATTATTTGTGGCTGTTCACTACCATTACAGCATTGTTGGT

AGTAGGAATTAGGTCCAATCCTCCAGGTGGAGAGTGTGGAAAAACAA

CATGAATATGCTCTCTGTGATGACGGCTATTGTTGTAGTAACGCTGGATACT

GTGGTCAGACAGATGAGTATTGTGCCCCTGAAAACTGCCAAAGCCAA

TGTCGAACCCCATCTCCCCCACCACCACCACCTCCGCCCTTCACGCCACCAC

CTCCGGTTTCTCCCGATGATGTTAGTCACATCATTACTTCCTCGCTT

TTCGAGAAGATGCTCAAAAATCGAAATGATCCTCGATGCAAAAGTAAAGGC

TTCTACACTTACGACGCCTTCATAACTGCTGCTAGAAAATTTCCTGGA

TTTGGTACTACTGGCTCTCTTGAAACTCGTACAAGAGAACTAGCTGCGTTCT

TTGGCCAAACTTCTCACGAAACCACAGGAGGATGGTCATCTGCTGAT

CAGGGAGGACCATATGCCTGGGGATATTGCTATATCATAGAACAAGATGAT

CAATCTCCGCATTGCGTCGACAGCCTAGAATGGCCCTGTGTTCCTGGC

GAATTCTACTATGGTCGTGGACCCATCCAGATCAGTTAG

>Chitinase_contig69_920595
*Cannabis sativa* Jamaican Lion (v02-2019, unmasked: draft assembly), Name: EFW9900022332-RA, Type: CDS, Feature Location: (Chr: contig69, complement(join(920595..920752, 920949..921423))) Genomic Location: 920595-921423
(SEQ ID NO. 10)

MKYSYYLWLFTTITALLVVGIRSNPPGGECGKQHEYALCDDGYCCSNAGYCGQ

TDEYCAPENCQSQCRTPSPPPPPPPPFTPPPPVSPDDVSHIITSSL

FEKMLKNRNDPRCKSKGFYTYDAFITAARKFPGFGTTGSLETRTRELAAFFGQT

-continued

SHETTGGWSSADQGGPYAWGYCYIIEQDDQSPHCVDSLEWPCVPG

EFYYGRGPIQIS

>Chitinase_contig69_920595
*Cannabis sativa* Jamaican Lion (v02-2019, unmasked: draft assembly), Name: EFW9900022332-RA, Type: CDS, Feature Location: (Chr: contig69, complement(join(920595..920752, 920949..921423))) Genomic Location: 920595-921423

(SEQ ID NO. 11)

ATGAAATACTCTTATTATTTGTGGCTGTTCACTACCATTACAGCATTGTTGGT

AGTAGGAATTAGGTCCAATCCTCCAGGTGGAGAGTGTGGAAAACAA

CATGAATATGCTCTCTGTGATGACGGCTATTGTTGTAGTAACGCTGGATACT

GTGGTCAGACAGATGAGTATTGTGCCCCTGAAAACTGCCAAAGCCAA

TGTCGAACCCCATCTCCCCCACCACCACCACCTCCGCCCTTCACGCCACCAC

CTCCGGTTTCTCCCGATGATGTTAGTCACATCATTACTTCCTCGCTT

TTCGAGAAGATGCTCAAAAATCGAAATGATCCTCGATGCAAAAGTAAAGGC

TTCTACACTTACGACGCCTTCATAACTGCTGCTAGAAAATTTCCTGGA

TTTGGTACTACTGGCTCTCTTGAAACTCGTACAAGAGAACTAGCTGCGTTCT

TTGGCCAAACTTCTCACGAAACCACAGGAGGATGGTCATCTGCTGAT

CAGGGAGGACCATATGCCTGGGGATATTGCTATATCATAGAACAAGATGAT

CAATCTCCGCATTGCGTCGACAGCCTAGAATGGCCCTGTGTTCCTGGC

GAATTCTACTATGGTCGTGGACCCATCCAGATCAGTTAG

>Chitinase_contig2033_1331224
*Cannabis sativa* Jamaican Lion (v02-2019, unmasked: draft assembly), Name: EFW9900020898-RA, Type: CDS, Feature Location: (Chr: contig2033, join(1331455..1332472, 1332605..1332627)) Genomic Location: 1331455-1332627

(SEQ ID NO. 12)

MASPKYQIGYWLASKEKLFSSENKSIVSSFTHLYYAFLQVKNDTGELIIPPELEN

DMKSFVKSAHDNQKKALVSIGGPKTSDDNDPSSAISMMAKSAEK

RNKFVESTLAFAKDFSFDGFELAWEYPKTANDMRNLSNLFNSWKSSLNSCNDN

RKNLLLSIAVYCKPIIPNATSKQEIKYPSELENYVDIFNIILYNYC

PVTCPHSQFKPSNPGPNNSSEDSINSWLATNDFSTCKLVMGIPLYGNKWTLADE

NDSSIGAPTIAYSGPIAYKDIPDPEGGIYDKDVTKCMYKADKNTW

YGYEASESINEKVEYAKKHLGGYFLYAIGDDDDGQTMCIAAAEQMAARE

>Chitinase_conitg2033_1331224
*Cannabis sativa* Jamaican Lion (v02-2019, unmasked: draft assembly), Name: EFW9900020898-RA, EFW9900020898, maker-contig2033-augustus-gene-3.174-mRNA-1, Type: mRNA, Feature Location: (Chr: contig2033, join(1331224..1331321, 1331443..1331454, 1331443..1332472, 1332605..1333115, 1332628..1333115)) Genomic Location: 1331224-1333115

(SEQ ID NO. 13)

GCACTTGACATGATAAGAAAAACTCTATAAATAGCATGGGATATTCAAGTG

AACAAACACACCACTACAAAAAACCTAATTATATATCATTTTTATAGT

TGTACCATATAATGGCATCTCCGAAGTACCAAATCGGTTACTGGCTTGCATC

CAAAGAAAAATTATTTTCATCTGAAAATAAGTCTATTGTATCCTCAT

TTACTCACCTGTATTATGCCTTTCTTCAGGTTAAAAATGATACCGGAGAGCT

GATTATCCCTCCCGAACTTGAGAATGATATGAAGTCTTTTGTCAAGA

GTGCTCATGACAACCAAAAGAAAGCTCTAGTGTCTATTGGAGGCCCGAAAA

CAAGCGATGACAATGACCCTTCCTCCGCTATCTCTATGATGGCAAAGA

GCGCTGAAAAACGTAACAAGTTTGTTGAATCGACCTTAGCTTTCGCTAAAGA

-continued

CTTTAGCTTTGATGGTTTTGAGCTTGCTTGGGAATATCCTAAAACGG

CAAATGACATGAGAAACCTAAGCAATCTCTTCAACAGTTGGAAATCTTCTTT

GAATTCATGTAATGATAATAGAAAGAACCTACTACTCTCAATTGCGG

TTTATTGCAAACCCATTATTCCAAATGCTACTTCGAAACAAGAAATCAAATA

CCCTTCCGAACTCGAAAATTATGTTGACATTTTCAATATAATCCTCT

ACAATTATTGTCCAGTCACTTGTCCACATTCCCAATTCAAGCCTAGCAACCC

TGGCCCTAATAACAGCAGTGAAGACTCTATTAATAGTTGGCTCGCTA

CAAATGATTTTTCGACCTGTAAACTAGTTATGGGCATTCCCTTGTACGGAAA

TAAATGGACATTGGCTGATGAAAATGATTCCAGCATTGGGGCACCAA

CTATTGCCTATTCTGGTCCCATCGCGTATAAAGATATTCCTGATCCAGAAGG

TGGGATCTATGATAAGGATGTTACCAAGTGCATGTACAAGGCTGATA

AAAATACTTGGTATGGCTACGAAGCTTCAGAATCTATAAATGAAAAGGTCG

AGTATGCTAAGAAACATCTTGGTGGGTATTTCCTATATGCCATTGGGG

ATGATGATGATGGTCAAACCATGTGTATTGCAGCTGCAGAGCAAATGGCAG

CAAGAGAATGAAGATCTTGTTTTCCAATTATGAATGAGGGTGGATTTA

AATATATTTAAATAACAGCAAAGTACACATAAAAACTTTGCACCAATAAAC

CACCTTGATCACTTTTATCTGTTTTTGTATTGTATTGTGTAATAAATT

AAAGGCCTATTCGTTGGTCCTTTTCGTGCAAGAGAGGAATCTCGACCACCTT

ATCTTGGTGTAAGAGTAACTTCATTTTGCACTAGTACCTAATAAGAT

TGTCATTGTTTGTGTGCTTTTTAGTTTTATGTGTCATGAAATAAATGAATAAG

GATTGTGTATCTTTTGAAGTTTTTCTTTGCATAATGTTTTGCCCCT

TGCACTAAAATGAATGGGATGAGGAAACATGTTAGCATCATTAAAGCAAAA

CAGAAGAAATAGCATAATTAATATGAGGAATAGTCTCTGGAAGCTTTA

TTGAATAAGTAAAAGGAGACCAAGGTCTCTTACATATATTATTGTATAGCAT

CACAGATCTTGTTTTCCAATTATGAATGAGGGTGGATTTAAATATAT

TTAAATAACAGCAAAGTACACATAAAAACTTTGCACCAATAAACCACCTTG

ATCACTTTTATCTGTTTTTGTATTGTATTGTGTAATAAATTAAAGGCC

TATTCGTTGGTCCTTTTCGTGCAAGAGAGGAATCTCGACCACCTTATCTTGG

TGTAAGAGTAACTTCATTTTGCACTAGTACCTAATAAGATTGTCATT

GTTTGTGTGCTTTTTAGTTTTATGTGTCATGAAATAAATGAATAAGGATTGT

GTATCTTTTGAAGTTTTTCTTTGCATAATGTTTTGCCCCTTGCACTA

AAATGAATGGGATGAGGAAACATGTTAGCATCATTAAAGCAAAACAGAAG

AAATAGCATAATTAATATGAGGAATAGTCTCTGGAAGCTTTATTGAATA

AGTAAAAGGAGACCAAGGTCTCTTACATATATTATTGTATAGCATCAC

Chitinase contig87_549179
*Cannabis sativa* Jamaican Lion (v02-2019, unmasked: draft assembly), Name: EFW9900022078-RA, Type: CDS, Feature Location: (Chr: contig87, complement join(549179..549578, 549692..549845, 550626..551034))) Genomic Location: 549179-551034

(SEQ ID NO. 14)

MKICALTIVSLLLLTIEGGSAEQCGRQAGGALCPGGLCCSEFGWCGNTPDYCND

KCQSQCGSSPGGGGLGGLISRATFDNMLKHRNDGACPARNFYTYD

AFISAAKAFPGFGNTGDDATKKREIAAFLAQTSHETTGGWPTAPDGPHSWGYC

FVRERNPPSDYCRSDATYPCAPGRQYYGRGPMQLSWNYNYGQCGRA

-continued

IGVDLLNNPDLVATDPVISFKAAIWFWMTPQSPKPSCHDVITGRWNPSGADQA

AGRVPGYGVTTNIINGGLECGKGRNDQVEDRIGFFKRYCDIFRIGY

GNNLDCYNQRPWGNGLFQLDAVM

Chitinase contig87_549179
*Cannabis sativa* Jamaican Lion (v02-2019, unmasked: draft assembly), Name: EFW9900022078-RA, Type: CDS, Feature Location: (Chr: contig87, complement join(549179..549578, 549692..549845, 550626..551034))) Genomic Location: 549179-551034

(SEQ ID NO. 15)

ATGAAGATTTGTGCATTGACAATTGTGTCCCTGCTGTTGTTGACCATAGAAG

GAGGGTCAGCAGAGCAATGTGGAAGACAAGCTGGGGGTGCTCTGTGT

CCAGGGGGGCTGTGCTGCAGCGAATTTGGGTGGTGTGGCAACACACCCGAT

TACTGCAACGATAAATGCCAAAGCCAATGCGGATCAAGTCCTGGGGGT

GGGGGCCTTGGTGGTCTAATTTCAAGGGCCACTTTTGATAATATGCTTAAGC

ATCGTAACGATGGTGCTTGTCCTGCTAGAAACTTTTACACTTACGAC

GCTTTCATCTCCGCTGCTAAAGCTTTTCCTGGCTTCGGCAACACTGGTGATG

ATGCAACTAAGAAAAGGGAGATCGCTGCTTTCTTAGCCCAAACTTCC

CACGAAACTACAGGTGGATGGCCAACGGCACCTGATGGCCCACATTCTTGG

GGATACTGCTTCGTGAGGGAGCGAAATCCACCAAGCGATTACTGTAGA

TCTGACGCTACTTACCCTTGTGCTCCCGGAAGGCAATACTATGGCCGTGGTC

CAATGCAACTTTCATGGAACTACAACTACGGACAATGTGGAAGAGCC

ATTGGAGTGGACCTACTGAACAATCCAGACCTTGTAGCTACGGACCCTGTA

ATTTCTTTCAAGGCAGCAATCTGGTTCTGGATGACCCCACAGTCACCG

AAGCCATCCTGCCATGACGTCATCACCGGGAGATGGAATCCCTCCGGGGCT

GATCAGGCCGCCGGTAGAGTCCCCGGTTACGGTGTGACGACGAACATC

ATCAACGGCGGGCTTGAGTGCGGGAAAGGCCGGAACGATCAGGTGGAAGA

CCGAATTGGGTTCTTTAAGAGGTACTGTGATATATTCCGGATTGGGTAC

GGAAATAATTTGGACTGTTACAACCAAAGGCCTTGGGGAAATGGACTCTTC

CAGCTGGATGCGGTCATGTAA

Chitinase_contig13_4567616
>*Cannabis sativa* Jamaican Lion(v02-2019, unmasked: draft assembly), Name: EFW9900002926-RA, Type: CDS, Feature Location: (Chr: contig13, complement(join(4567616..4567952, 4568175..4568322, 4568436..4569048))) Genomic Location: 4567616-4569048

(SEQ ID NO. 16)

MKLSNLLTLFSLSCLSVLLVGNIVSTDGAQCGRQAGGALCRNNLCCSQWGFCG

STEAYCGAGCQSQCWNERPDHRCGAGTGNSPCAPGRCCSRFGFCGS

TAAYCQGNNCQYQCWRIAPSTDELIRAMLGDYNANDDSDIRNVISESIFNEMFK

HRKDCPSKGFYDYQSFVIAAASFPGFGTTGDVATRKREIAAFFAQ

TSHATAGKWIDSFDQHAWGYCFINRTAGEYDYCTSSHWPCAAGKKYNSRGPIQ

LTHNYNYGLASEALGIDLINNPELVATDSVVSFKTAVWYWMTQHDN

NPSFHNIVINANSGIKNQLPTYANTNNDKNLVGYYKRYCDMLRVSYGDNLDYL

SKFPNASGISMLSQI

Chitinase_contig13_4567616
*Cannabis sativa* Jamaican Lion (v02-2019, unmasked: draft assembly), Name: EFW9900002926-RA, Type: CDS, Feature Location: (Chr: contig13, complement(join(4567616..4567952, 4568175..4568322, 4568436..4569048))) Genomic Location: 4567616-4569048

(SEQ ID NO. 17)

ATGAAGTTAAGCAACCTTCTTACACTCTTTTCCCTTTCCTGTCTTTCTGTTTTG

CTAGTGGGGAATATTGTCTCTACAGATGGAGCCCAATGTGGAAGA

CAGGCAGGCGGGGCCTTGTGTCGAAATAACCTCTGTTGTAGCCAATGGGGT

TTTTGTGGTAGCACAGAAGCCTATTGTGGAGCTGGTTGTCAAAGTCAA

TGTTGGAATGAAAGACCTGATCACAGATGTGGGGCTGGCACTGGAAACAGT

CCATGCGCTCCAGGAAGGTGTTGTAGCAGATTTGGGTTTTGTGGTAGC

ACAGCTGCTTATTGCCAAGGAAACAATTGTCAATACCAATGTTGGAGAATT

GCACCTTCCACTGATGAACTCATTCGTGCTATGCTCGGAGATTATAAC

GCCAATGATGATTCAGATATAAGAAATGTTATTAGTGAATCAATCTTCAACG

AAATGTTTAAGCATAGAAAGGATTGCCCAAGTAAAGGTTTCTACGAT

TACCAGTCTTTTGTCATTGCTGCTGCCTCTTTCCCTGGTTTTGGTACCACTGG

AGATGTGGCAACTCGTAAAAGGGAAATCGCAGCTTTCTTTGCTCAA

ACATCTCATGCAACTGCAGGAAAATGGATTGATTCATTTGATCAACATGCAT

GGGGATATTGCTTTATCAATAGAACTGCTGGCGAGTATGATTATTGT

ACATCTTCTCATTGGCCATGTGCTGCTGGCAAAAAATATAATAGTCGAGGAC

CAATTCAACTTACCCACAACTACAACTATGGGCTTGCTAGTGAAGCA

CTGGGAATAGATTTGATAAACAATCCTGAATTGGTAGCAACAGACTCAGTG

GTGTCGTTCAAAACTGCCGTATGGTATTGGATGACTCAACATGATAAC

AACCCTTCATTCCACAACATTGTTATCAATGCAAATTCTGGAATTAAAAACC

AACTCCCAACTTATGCTAATACCAATAATGACAAAAACCTTGTTGGG

TACTATAAAAGGTACTGTGACATGTTAAGGGTGAGTTATGGAGATAACTTA

GACTATTTGTCTAAGTTTCCTAACGCCTCTGGCATTTCTATGCTTTCC

CAGATCTGA

>*Cannabis sativa* Jamaican Lion (v02-2019, unmasked: draft assembly), Name: EFW9900002926-RA, Type: CDS, Feature Location: (Chr: contig13, complement join(4567616..4567952, 4568175..4568322, 4568436..4569048))) Genomic Location: 4567616-4569048

(SEQ ID NO. 18)

MKLSNLLTLFSLSCLSVLLVGNIVSTDGAQCGRQAGGALCRNNLCCSQWGFCG

STEAYCGAGCQSQCWNERPDHRCGAGTGNSPCAPGRCCSRFGFCGS

TAAYCQGNNCQYQCWRIAPSTDELIRAMLGDYNANDDSDIRNVISESIFNEMFK

HRKDCPSKGFYDYQSFVIAAASFPGFGTTGDVATRKREIAAFFAQ

TSHATAGKWIDSFDQHAWGYCFINRTAGEYDYCTSSHWPCAAGKKYNSRGPIQ

LTHNYNYGLASEALGIDLINNPELVATDSVVSFKTAVWYWMTQHDN

NPSFHNIVINANSGIKNQLPTYANTNNDKNLVGYYKRYCDMLRVSYGDNLDYL

SKFPNASGISMLSQI

Quantitative PCR assay for detection of RNA and DNA.

CsTLP1_2563 F (SEQ ID NO. 19)
CCT CCA ACA ACT CTG GTC GAA ATA AC

CsTLP1_2563 R (SEQ ID NO. 20)
CAC CTT CTG GCC TA A CCG AAA C

CsTLP1_2563_Probe (SEQ ID NO. 21)
/5Cy5/AG CAA CGT GGA CGG GTT CAA CTT A/3IAbRQSp/

>CsTLP1_v2_forward_primer (SEQ ID NO. 22)
AGTCAAACTGATAGAGATTGGAAC

>CsTLP1_v2_probe (SEQ ID NO. 23)
/5Cy5/TGCAATGTAGTTGCAGGTGGTTT/3IAbRQSp/

>CSTLP1_v2_reverse_primer (SEQ ID NO. 24)
GCCAATTTCTTGGCCTCTAC

CsTLP4_81_1172664 F (SEQ ID NO. 25)
TCC ACA GAC CCA ACA ACA TC

CsTLP4_81_1172664 R (SEQ ID NO. 26)
TAG AGT CGC CGG AGG AAT AG

CsTLP4_81_1172664 Probe (SEQ ID NO. 27)
/56-FAM/AT TGT GGC T/ZEN/C CTC CAC CGT TGA AT/3IABKFQ/

Genomic_Control_1F (SEQ ID NO. 28)
TACACGACGTTGTAAAACGACCCAGATGCTAACTGCACGA

Genomic_Control_1R (SEQ ID NO. 29)
AGGATAACAATTTCACACAGGGACTTCTCCTGACCTGACCA

Genomic_Control_Probe_v4 (SEQ ID NO. 30)
/5HEX/AACAGTATG/ZEN/GCCAAATGGTCAGGT/3IABkFQ/

CsTLP2_93_3888473_F (SEQ ID NO. 31)
CGTGTACGGGAGCTGATTATAC

CsTLP2_93_3888473_R (SEQ ID NO. 32)
GGGTTGTTGCTGTTGTTGTC

CsTLP3_93_3888473_Probe (SEQ ID NO. 33)
/5TEX615/AGATACTACGCCAACAGCAGCAGG/3AbRQSp/

REFERENCES

1. Victory K R, Couch J, Lowe B, Green B J. Notes from the Field: Occupational Hazards Associated with Harvesting and Processing *Cannabis*—Washington, 2015-2016. MMWR Morbidity and mortality weekly report. 2018 Mar. 2; 67 (8): 259-60. PubMed PMID: 29494573. Pubmed Central PMCID: 5861698.
2. Zamir. *Fusarium* and *Pythium* species infecting roots of hydroponically grown marijuana (*Cannabis sativa* L.) plants. Canadian Journal of Plant Pathology. 2018.
3. Wahby C, Ligero. *Agrobacterium* infection of hemp (*Cannabis sativa* L.): establishment of hairy root cultures. Journal of Plant Interactions. 2013; 8:4, 312-320.
4. Šķipars V, Rauda, E., Snepste, I. et al. Assessment of gene copy number variation of Scots pine thaumatin-like protein gene using real-time PCR based methods. Tree Genetics & Genomes. 17 Nov. 2017; 13:127.
5. Grenier J, Potvin C, Trudel J, Asselin A. Some thaumatin-like proteins hydrolyse polymeric beta-1,3-glucans. The Plant journal: for cell and molecular biology. 1999 August; 19 (4): 473-80. PubMed PMID: 10504569.
6. Trudel J, Grenier J, Potvin C, Asselin A. Several thaumatin-like proteins bind to beta-1,3-glucans. Plant physiology. 1998 December; 118 (4): 1431-8. PubMed PMID: 9847118. Pubmed Central PMCID: 34760.
7. Adams D J. Fungal cell wall chitinases and glucanases. Microbiology. 2004 July; 150 (Pt 7): 2029-35. PubMed PMID: 15256547.
8. Mackintosh C A, Lewis J, Radmer L E, Shin S, Heinen S J, Smith L A, et al. Overexpression of defense response genes in transgenic wheat enhances resistance to *Fusarium* head blight. Plant cell reports. 2007 April; 26 (4): 479-88. PubMed PMID: 17103001. Pubmed Central PMCID: 1824786.
9. Larramendi C H, Lopez-Matas M A, Ferrer A, Huertas A J, Pagan J A, Navarro L A, et al. Prevalence of sensitization to *Cannabis sativa*. Lipid-transfer and thaumatin-like proteins are relevant allergens. International archives of allergy and immunology. 2013; 162 (2): 115-22. PubMed PMID: 23921252.
10. Orsburn. The First Publicly Available Annotated Genome for *Cannabis* plants. BioRXIV. 2019; 786186.
11. Punja Z K. Flower and foliage-infecting pathogens of marijuana (*Cannabis sativa* L.) plants. Canadian Journal of Plant Pathology 2018.
12. Gent D H, Claassen B J, Twomey M C, Wolfenbarger S N, Woods J L. Susceptibility of Hop Crown Buds to Powdery Mildew and its Relation to Perennation of *Podosphaera macularis*. Plant disease. 2018 July; 102 (7): 1316-25. PubMed PMID: 30673566.
13. Gent D H, Massie S T, Twomey M C, Wolfenbarger S N. Adaptation to Partial Resistance to Powdery Mildew in the Hop Cultivar Cascade by *Podosphaera macularis*. Plant disease. 2017 June; 101 (6): 874-81. PubMed PMID: 30682923.
14. Wolfenbarger S N, Massie S T, Ocamb C, Eck E B, Grove G G, Nelson M E, et al. Distribution and Characterization of *Podosphaera macularis* Virulent on Hop Cultivars Possessing R6-Based Resistance to Powdery Mildew. Plant disease. 2016 June; 100 (6): 1212-21. PubMed PMID: 30682268.
15. Gent D H, Twomey M C, Wolfenbarger S N, Woods J L. Pre- and Postinfection Activity of Fungicides in Control of Hop Downy Mildew. Plant disease. 2015 June; 99 (6): 858-65. PubMed PMID: 30699537.
16. Twomey M C, Wolfenbarger S N, Woods J L, Gent D H. Development of partial ontogenic resistance to powdery mildew in hop cones and its management implications. PloS one. 2015; 10 (3): e0120987. PubMed PMID: 25811173. Pubmed Central PMCID: 4374666.
17. Wolfenbarger S N, Eck E B, Ocamb C M, Probst C, Nelson M E, Grove G G, et al. Powdery Mildew Outbreaks caused by *Podosphaera macularis* on Hop Cultivars Possessing the Resistance Gene R6 in the Pacific Northwestern United States. Plant disease. 2014 June; 98 (6): 852. PubMed PMID: 30708655.
18. Misra R C, Sandeep, Kamthan M, Kumar S, Ghosh S. A thaumatin-like protein of *Ocimum basilicum* confers tolerance to fungal pathogen and abiotic stress in transgenic

*Arabidopsis*. Scientific reports. 2016 May 6; 6:25340. PubMed PMID: 27150014. Pubmed Central PMCID: 4858651.

Aghazadeh. 2016. Co-transformation of canola by chimeric chitinase and tlp genes towards improving resistance to *Sclerotinia sclerotiorum. World J Microbiol Biotechnol* September; 32 (9): 144.

Allen K D, McKernan K, Pauli C, Roe J, Torres A, Gaudino R. 2019. Genomic characterization of the complete terpene synthase gene family from *Cannabis sativa. PloS one* 14: e0222363.

Andre C M, Hausman J F, Guerriero G. 2016. *Cannabis sativa*: The Plant of the Thousand and One Molecules. *Frontiers in plant science* 7:19.

Backer R, Schwinghamer T, Rosenbaum P, McCarty V, Eichhorn Bilodeau S, Lyu D, Ahmed M B, Robinson G, Lefsrud M, Wilkins O et al. 2019. Closing the Yield Gap for *Cannabis*: A Meta-Analysis of Factors Determining *Cannabis* Yield. *Frontiers in plant science* 10:495.

Clarke. 2017. *Cannabis* Domestication, Breeding History, Present-day Genetic Diversity, and Future Prospects. *CRITICAL REVIEWS IN PLANT SCIENCES doi: http://dx.doi.org/*10.1080/07352689.2016.1267498.

Cottier F, Sherrington S, Cockerill S, Del Olmo Toledo V, Kissane S, Tournu H, Orsini L, Palmer G E, Perez J C, Hall R A. 2019. Remasking of *Candida albicans* beta-Glucan in Response to Environmental pH Is Regulated by Quorum Sensing. *mBio* 10.

Fraczek M G, Zhao C, Dineen L, Lebedinec R, Bowyer P, Bromley M, Delneri D. 2019. Fast and Reliable PCR Amplification from *Aspergillus fumigatus* Spore Suspension Without Traditional DNA Extraction. *Curr Protoc Microbiol* 54: e89.

Fredricks D N, Smith C, Meier A. 2005. Comparison of six DNA extraction methods for recovery of fungal DNA as assessed by quantitative PCR. *J Clin Microbiol* 43:5122-5128.

Garcia-Rubio R, de Oliveira H C, Rivera J, Trevijano-Contador N. 2019. The Fungal Cell Wall: *Candida, Cryptococcus*, and *Aspergillus* Species. *Frontiers in microbiology* 10:2993.

Gent D H, Claassen B J, Twomey M C, Wolfenbarger S N, Woods J L. 2018. Susceptibility of Hop Crown Buds to Powdery Mildew and its Relation to Perennation of *Podosphaera macularis. Plant disease* 102:1316-1325.

Gent D H, Massie S T, Twomey M C, Wolfenbarger S N. 2017. Adaptation to Partial Resistance to Powdery Mildew in the Hop Cultivar Cascade by *Podosphaera macularis. Plant disease* 101:874-881.

Gent D H, Twomey M C, Wolfenbarger S N, Woods J L. 2015. Pre- and Postinfection Activity of Fungicides in Control of Hop Downy Mildew. *Plant disease* 99:858-865.

Goldschmidt P, Degorge S, Merabet L, Chaumeil C. 2014. Enzymatic treatment of specimens before DNA extraction directly influences molecular detection of infectious agents. *PloS one* 9: e94886.

Harkess A, Mercati F, Abbate L, McKain M, Pires J C, Sala T, Sunseri F, Falavigna A, Leebens-Mack J. 2016. Retrotransposon Proliferation Coincident with the Evolution of Dioecy in Asparagus. *G3* 6:2679-2685.

Harkess A, Zhou J, Xu C, Bowers J E, Van der Hulst R, Ayyampalayam S, Mercati F, Riccardi P, McKain M R, Kakrana A et al. 2017. The asparagus genome sheds light on the origin and evolution of a young Y chromosome. *Nature communications* 8:1279.

Kusari. 2013. Endophytic fungi harbored in *Cannabis sativa* L.: diversity and potential as biocontrol agents against host plant-specific phytopathogens. *Fungal Divers* 60, 137-151.

Larramendi C H, Lopez-Matas M A, Ferrer A, Huertas A J, Pagan J A, Navarro L A, Garcia-Abujeta J L, Andreu C, Carnes J. 2013. Prevalence of sensitization to *Cannabis sativa*. Lipid-transfer and thaumatin-like proteins are relevant allergens. *International archives of allergy and immunology* 162:115-122.

Lee K K, Maccallum D M, Jacobsen M D, Walker L A, Odds F C, Gow N A, Munro C A. 2012. Elevated cell wall chitin in *Candida albicans* confers echinocandin resistance in vivo. *Antimicrobial agents and chemotherapy* 56:208-217.

Lyu D, Backer R, Robinson W G, Smith D L. 2019. Plant Growth-Promoting Rhizobacteria for *Cannabis* Production: Yield, Cannabinoid Profile and Disease Resistance. *Frontiers in microbiology* 10:1761.

Misra R C, Sandeep, Kamthan M, Kumar S, Ghosh S. 2016. A thaumatin-like protein of *Ocimum basilicum* confers tolerance to fungal pathogen and abiotic stress in transgenic *Arabidopsis. Scientific reports* 6:25340.

Mohan Ram H Y, Sett R. 1982. Induction of fertile male flowers in genetically female *Cannabis sativa* plants by silver nitrate and silver thiosulphate anionic complex. *TAG Theoretical and applied genetics Theoretische und angewandte Genetik* 62:369-375.

Penuelas J, Farre-Armengol G, Llusia J, Gargallo-Garriga A, Rico L, Sardans J, Terradas J, Filella I. 2014. Removal of floral microbiota reduces floral terpene emissions. *Scientific reports* 4:6727.

Prentout. 2019. A high-throughput segregation analysis identifies the sex chromosomes of *Cannabis sativa. BioRXIV doi: http://dx.doi.org/*10.1101/721324

Punja Z K. 2018. Flower and foliage-infecting pathogens of marijuana (*Cannabis sativa* L.) plants. *Canadian Journal of Plant Pathology* doi: https://doi.org/10.1080/07060661.2018.1535467.

Ruiz-Herrera J, Elorza M V, Valentin E, Sentandreu R. 2006. Molecular organization of the cell wall of *Candida albicans* and its relation to pathogenicity. *FEMS Yeast Res* 6:14-29.

Twomey M C, Wolfenbarger S N, Woods J L, Gent D H. 2015. Development of partial ontogenic resistance to powdery mildew in hop cones and its management implications. *PloS one* 10: e0120987.

Vujanovic. 2017. qPCR assessment of aurofusarin gene expression in mycotoxigenic *Fusarium* species challenged with mycoparasitic and chemical control agents. *Biological Control Volume* 109: Pages 51-57.

Wally O, Punja Z K. 2010. Genetic engineering for increasing fungal and bacterial disease resistance in crop plants. *GM crops* 1:199-206.

Wolfenbarger S N, Eck E B, Ocamb C M, Probst C, Nelson M E, Grove G G, Gent D H. 2014. Powdery Mildew Outbreaks caused by *Podosphaera macularis* on Hop Cultivars Possessing the Resistance Gene R6 in the Pacific Northwestern United States. *Plant disease* 98:852.

Wolfenbarger S N, Massie S T, Ocamb C, Eck E B, Grove G G, Nelson M E, Probst C, Twomey M C, Gent D H. 2016. Distribution and Characterization of *Podosphaera macularis* Virulent on Hop Cultivars Possessing R6-Based Resistance to Powdery Mildew. *Plant disease* 100:1212-1221.

What is claimed is:

1. A method of determining fungal burden of a *Cannabis* plant, the method comprising:

obtaining a sample collected from the *Cannabis* plant;

applying a lysis composition comprising an active *Cannabis* chitinase and an active *Cannabis* thaumatin-like protein (TLP) as lysing enzymes to the sample so as to lyse fungal cells when present in the sample, wherein the active *Cannabis* thaumatin-like protein (TLP) is from *Cannabis sativa* having at least 95% amino acid amino acid sequence identity to the full-length amino acid sequence as set forth in SEQ ID NO: 1;

extracting genomic DNA (gDNA) or RNA from the lysed sample; and detecting a quantity of a fungal gene sequence when present in the genomic DNA (gDNA) or RNA, wherein detection of the quantity of the fungal gene sequence is indicative of the fungal burden of the *Cannabis* plant.

2. The method of claim 1, wherein the active *Cannabis* chitinase and the active *Cannabis* TLP enzymatically digest chitin and glucan present in fungal cell walls, respectively.

3. The method of claim 1, wherein the active *Cannabis* TLP has β-1,3-glucanase activity.

4. The method of claim 1, wherein the active *Cannabis* thaumatin-like protein (TLP) comprises the amino acid sequence as set forth in SEQ ID NO: 1.

5. The method of claim 1, wherein the active *Cannabis* chitinase is *Cannabis sativa* chitinase.

6. The method of claim 1, wherein the fungal gene sequence is an 18S rRNA gene sequence.

7. The method of claim 1, wherein the fungal gene sequence is a conserved housekeeping gene sequence.

8. The method of claim 1, wherein the fungal cells comprise Ascomycota.

9. The method of claim 8, wherein the fungal cells comprise *Candida* species.

10. The method of claim 8, wherein the fungal cells comprise *Aspergillus* species.

11. The method of claim 8, wherein the fungal cells comprise Golovinomyces *cichoracearum*.

12. The method of claim 1, wherein the sample is incubated with the lysis composition for 10 minutes to 60 minutes at a temperature between 25° C. and 37° C.

13. The method of claim 1, wherein the lysing enzymes have concentrations from 0.1 unit/mL to 106 units/mL.

* * * * *

SEQUENCE LISTING

<160> NUMBER OF SEQ ID NOS: 33

<210> SEQ ID NO 1
<211> LENGTH: 225
<212> TYPE: PRT
<213> ORGANISM: Escherichia coli

<400> SEQUENCE: 1

```
Met Ile Gln Asn Asn Cys Gly Arg Thr Ile Trp Pro Ala Thr Gln Ser
1               5                   10                  15

Gly Ser Gly Ser Ser Gln Leu Ser Thr Thr Gly Phe Glu Leu Ala Ser
            20                  25                  30

Gly Ala Ser Gln Ser Ile Glu Ile Pro Ala Gly Pro Trp Ser Gly Arg
        35                  40                  45

Phe Trp Gly Arg Asp Gly Cys Ser Thr Asp Ser Ser Gly Arg Phe Ala
    50                  55                  60

Cys Ala Ser Gly Asp Cys Ala Ser Gly Thr Val Glu Cys Asn Gly Ala
65                  70                  75                  80

Gly Gly Val Pro Pro Thr Thr Leu Val Glu Ile Thr Val Ala Glu Asn
                85                  90                  95

Gly Gly Gln Asp Phe Tyr Asp Val Ser Asn Val Asp Gly Phe Asn Leu
            100                 105                 110

Pro Val Ser Val Arg Pro Glu Gly Gly Asn Gly Asp Cys Gln Glu Ser
        115                 120                 125

Thr Cys Pro Asn Asn Leu Asn Asp Gly Cys Pro Ala Asp Leu Gln Tyr
    130                 135                 140

Lys Ser Gly Asp Asp Val Val Gly Cys Leu Ser Ser Cys Ala Lys Tyr
145                 150                 155                 160

Asn Met Asp Gln Asp Cys Cys Arg Gly Ala Tyr Asp Ser Pro Asp Thr
                165                 170                 175

Cys Thr Pro Ser Glu Ser Ala Asn Tyr Phe Glu Gln Gln Cys Pro Gln
            180                 185                 190

Ala Tyr Ser Tyr Ala Tyr Asp Asp Lys Thr Ser Thr Phe Thr Cys Ser
        195                 200                 205

Gly Gly Pro Asn Tyr Leu Ile Thr Phe Cys Pro His His His His His
    210                 215                 220

His
225
```

<210> SEQ ID NO 2
<211> LENGTH: 225
<212> TYPE: PRT
<213> ORGANISM: Cannabis sativa

<400> SEQUENCE: 2

```
Met His His His His His His Ile Gln Asn Asn Cys Gly Arg Thr Ile
1               5                   10                  15

Trp Pro Ala Thr Gln Ser Gly Ser Gly Ser Ser Gln Leu Ser Thr Thr
            20                  25                  30

Gly Phe Glu Leu Ala Ser Gly Ala Ser Gln Ser Ile Glu Ile Pro Ala
        35                  40                  45

Gly Pro Trp Ser Gly Arg Phe Trp Gly Arg Asp Gly Cys Ser Thr Asp
    50                  55                  60

Ser Ser Gly Arg Phe Ala Cys Ala Ser Gly Asp Cys Ala Ser Gly Thr
65                  70                  75                  80

Val Glu Cys Asn Gly Ala Gly Gly Val Pro Pro Thr Thr Leu Val Glu
```

-continued

```
                85                  90                  95

Ile Thr Val Ala Glu Asn Gly Gly Gln Asp Phe Tyr Asp Val Ser Asn
            100                 105                 110

Val Asp Gly Phe Asn Leu Pro Val Ser Val Arg Pro Glu Gly Gly Asn
        115                 120                 125

Gly Asp Cys Gln Glu Ser Thr Cys Pro Asn Asn Leu Asn Asp Gly Cys
    130                 135                 140

Pro Ala Asp Leu Gln Tyr Lys Ser Gly Asp Asp Val Val Gly Cys Leu
145                 150                 155                 160

Ser Ser Cys Ala Lys Tyr Asn Met Asp Gln Asp Cys Cys Arg Gly Ala
                165                 170                 175

Tyr Asp Ser Pro Asp Thr Cys Thr Pro Ser Glu Ser Ala Asn Tyr Phe
            180                 185                 190

Glu Gln Gln Cys Pro Gln Ala Tyr Ser Tyr Ala Tyr Asp Asp Lys Thr
        195                 200                 205

Ser Thr Phe Thr Cys Ser Gly Gly Pro Asn Tyr Leu Ile Thr Phe Cys
    210                 215                 220

Pro
225


<210> SEQ ID NO 3
<211> LENGTH: 738
<212> TYPE: DNA
<213> ORGANISM: Cannabis sativa

<400> SEQUENCE: 3

atgaagattc aaataatact cttctttact gtcgccctag ctttaatctt tgctgcaggg      60

acgaatgcag ctaccgtcaa cattcaaaac aactgcggaa gaaccatctg gccagcaacc     120

caatccggca gcggaagttc acaactctca accactggtt tcgagttagc atcaggagcc     180

agccagtcca tcgaaatccc agccggacca tggtcggggc gcttctgggg tcgagatggt     240

tgctccactg actcatccgg caggttcgcg tgcgctagcg gagactgtgc ctctggtacg     300

gtggagtgta atggtgcagg cggagtccct ccaacaactc tggtcgaaat aaccgttgca     360

gaaaacggtg gacaagattt ctacgacgtg agcaacgtgg acgggttcaa cttaccggtt     420

tcggttaggc cagaaggtgg taatggggat tgccaggagt caacgtgccc aaacaaccta     480

aacgacggtt gcccagctga tctacagtac aaatccggag acgacgtcgt tgggtgcctc     540

agctcttgcg ccaagtataa tatggaccaa gactgttgta gaggagctta tgattctcca     600

gacacgtgta ctcctagtga gtccgctaac tacttcgagc aacaatgccc tcaggcttac     660

agctatgctt atgatgataa gaccagcact tttacttgct ccggtggacc taactatctt     720

atcactttct gcccatga                                                   738


<210> SEQ ID NO 4
<211> LENGTH: 1026
<212> TYPE: DNA
<213> ORGANISM: Cannabis sativa

<400> SEQUENCE: 4

atggatcctt attcaaggtt ctcattttca ctcattctca gctttgtcgt cctacttctc      60

acctccagag gcgtcacagc tgccaccttt aacttcgtta atcgatgtga ctacactgtt     120

tggccgggca ttctagctaa tgccggaagc ccaagactcg acagcacagg attcgagcta     180

ccaaaggaca cctctcgatc tttcctggct ccgacgggtt ggtcgggtcg tttttggggt     240
```

```
cggacgggtt gtacttttga tgaatcagga tccgggtcct gtctcaccgg agactgtggt     300

tctggcgtgg tcgagtgcaa cggcgccgga gctgcaccgc cagcgaccct cgccgagttc     360

actttaggaa ccggcgggca ggacttctac gacgtcagcc tcgtcgacgg ctataacttg     420

cccatggtcg ttgaaggaac tggcgggtcg ggcctgtgcg cctccacggg ttgccccacc     480

gacttgaacc agcaatgccc gtcggagttg agggtcggga acggtaacgc gtgtaagagc     540

gcgtgcgagg ctttcgggac cccagaatac tgttgcagcg gcgcgtatgg tacacccgcc     600

acttgtaggc cgtcagttta ctctgagatg tttaagtccg cgtgtcccag atcgtatagc     660

tacgcctacg atgatgccac cagtacgttt acgtgtacgg gagctgatta tacggtgacg     720

ttttgtccat cttcaccaag ccaaaaatcc acaagagata ctacgccaac agcagcaggg     780

tcacaatccg ggcaacgta ttcggatcca ggacaacaac agcaacaacc cgaggtaaca     840

tatccagaag caggatccgg gtcgggtact ggaagtggat ccggaggaac ccttttagca     900

gatgggacat ggttggctgg tttggcaatg ggagactcac caagaacagt cttatcaccc     960

tcaactctac gtgttgcact catagccttt gtagcttttt attccatctt attaagaaag    1020

ttgtaa                                                               1026
```

```
<210> SEQ ID NO 5
<211> LENGTH: 951
<212> TYPE: DNA
<213> ORGANISM: Cannabis sativa

<400> SEQUENCE: 5

atggatcgga tcattcttac cgggtcactt ctcacactcc tcactttctc tttcgtctta      60

gaaatagagt caacgtcgtt caaattagta aacaaatgca ggaacaccat atggcccggc     120

ttgttatccg gtgccaactc agctccgctc cccaccaccg gcttcgttct ccacagcggc     180

gaatcccgga ccttacgcat acccagagcg tggtcgggtc gtctatgggc tcggacccat     240

tgcggccacg actcaaccgg gaaattcact tgcatcgccg gggactgcgg ctcaggcaag     300

ctggagtgtg aaggagccgg ggccaagccg ccagctacac tagctgagtt cactcttaac     360

ggcgcagacg gcttggactt ctacgacgtc agcttagtcg acgggtacaa catcccgatg     420

ttgatcgtcc ccaagggagg tacaagaggt ggatgcggcg ccaccggttg tctcgtcgac     480

ttaaacgggg cttgtccgac cgcgttgcga gtggcgcgtg ctaatggcaa agggagcgta     540

gcgtgtagga gcgcgtgtga agcgttcggg gatccccgct tctgttgtag tgaggcgtac     600

tctacacctg acacgtgtgg accttctcct tattcgctct acttcaaaca cgcttgccca     660

cgctcgtata gctacgcgta cgatgacaaa accagcactt acacgtgcgc ctccgctgat     720

tatactatta tattttgccc attaccctat acgagccaga aagtgttggg agcaagaaaa     780

gatgggatac cactaccact ggtgaataag accatgatgt acttaagaag ccgacactca     840

agcggagctg cagcatcgtc cacaggtctt tcttctttgc tatttatggc ccttgcagcc     900

actaatgcac tgccactttt gctatcatgg ccaatttata actctttgtg a              951
```

```
<210> SEQ ID NO 6
<211> LENGTH: 894
<212> TYPE: DNA
<213> ORGANISM: Cannabis sativa

<400> SEQUENCE: 6

atggcttctc ttcatcaatt tctcctcttc tctctaatca ttcccttctt ccatttcctt      60

caaggtgtta attcagctac attcacaatc acaaacgaat gcagttacac aatttggccg     120
```

```
ggaattttat ccggtgccgg aacttcacca ctttccacca ctggattttc tctccaaccg    180

ggagaatcaa actctctcca agtaccaatt tcttggtcag gtcgattatg ggtcgaacc    240

ctttgctcca cagacccaac aacatccaaa ttctcctgcg tcacaggcga ttgtggctcc    300

tccaccgttg aatgcagcgg tgccggagct attcctccgg cgactctagc tgaattcaca    360

cttaacggcg ctggaggatt ggatttctac gatgttagcc ttgttgacgg ttataacctc    420

cccatgaagg ttgctccggt ggtcggtgaa ggtaccggcg ggaactgtac tacgacgggt    480

tgtttggtgg atttgaatcc agggtgtccg gcggaattga aggtttcgtc ggcgagtgtg    540

gagagcgtgg cgtgtaaaag cgcgtgtgag gcttttgggg acccacagtt ttgttgtagt    600

ggggcctacg ctactcctga cacgtgtaaa cctagctctt attctctatt ctttaaaaat    660

gcgtgtccaa aagcttatag ctacgcttat gacgatggaa ccagtacctt cacatgtgcc    720

aacgccaatt acgtaattac cttttgccct tcgccaacta caagtgtaaa gtcttctaac    780

gggaagtatc ccgaggcagc cgaagtatcg gccagttctc gcaaaacgac accgtatctc    840

attggatttg gcgttttagg ggcaagttgg ggatttcggc aactattcat ttaa          894
```

<210> SEQ ID NO 7
<211> LENGTH: 555
<212> TYPE: DNA
<213> ORGANISM: Cannabis sativa

<400> SEQUENCE: 7

```
atgacggtta tttgtagtaa cgctggatac tgtggccaga cagatgccta ttgtgcccct     60

gaaaactgcc aaagccaatg tcgaacccca tctcccccac caccaccgtc accgccacct    120

cctcccttca cgccaccacc tccgatttct cccgatgatg atagtcacat cattacttcc    180

tcacttttcg aggagatgct tacctatcga aatgatcatc gatgcaaaag taatggcttc    240

tacacttacg acgccttcat aactgctgct agaatttttc cgggctttga tactactggc    300

tctcttgaaa ctcgtacaag agaactagct gcgttctttg gccaaacttc tcaggaaacc    360

acaggaatac atactggttt ggagtgcggc cacggtgttg atgaccgggt catagatagg    420

attggcttct atgaaaggta ctgccttata ctaggagtaa gcactgggga caatttggac    480

tgttacaatc aacgtccttt caatgatgat ccacaaacat cttatggagt cctcaaaatg    540

tctgttcaag aatag                                                     555
```

<210> SEQ ID NO 8
<211> LENGTH: 190
<212> TYPE: PRT
<213> ORGANISM: Cannabis sativa

<400> SEQUENCE: 8

```
Met His His His His His His Thr Val Ile Cys Ser Asn Ala Gly Tyr
1               5                   10                  15

Cys Gly Gln Thr Asp Ala Tyr Cys Ala Pro Glu Asn Cys Gln Ser Gln
            20                  25                  30

Cys Arg Thr Pro Ser Pro Pro Pro Pro Pro Ser Pro Pro Pro Pro Pro
        35                  40                  45

Phe Thr Pro Pro Pro Pro Ile Ser Pro Asp Asp Asp Ser His Ile Ile
    50                  55                  60

Thr Ser Ser Leu Phe Glu Glu Met Leu Thr Tyr Arg Asn Asp His Arg
65                  70                  75                  80

Cys Lys Ser Asn Gly Phe Tyr Thr Tyr Asp Ala Phe Ile Thr Ala Ala
```

```
                85                  90                  95

Arg Ile Phe Pro Gly Phe Asp Thr Thr Gly Ser Leu Glu Thr Arg Thr
            100                 105                 110

Arg Glu Leu Ala Ala Phe Phe Gly Gln Thr Ser Gln Glu Thr Thr Gly
        115                 120                 125

Ile His Thr Gly Leu Glu Cys Gly His Gly Val Asp Asp Arg Val Ile
    130                 135                 140

Asp Arg Ile Gly Phe Tyr Glu Arg Tyr Cys Leu Ile Leu Gly Val Ser
145                 150                 155                 160

Thr Gly Asp Asn Leu Asp Cys Tyr Asn Gln Arg Pro Phe Asn Asp Asp
                165                 170                 175

Pro Gln Thr Ser Tyr Gly Val Leu Lys Met Ser Val Gln Glu
            180                 185                 190


<210> SEQ ID NO 9
<211> LENGTH: 633
<212> TYPE: DNA
<213> ORGANISM: Cannabis sativa

<400> SEQUENCE: 9

atgaaatact cttattattt gtggctgttc actaccatta cagcattgtt ggtagtagga      60

attaggtcca atcctccagg tggagagtgt ggaaaacaac atgaatatgc tctctgtgat     120

gacggctatt gttgtagtaa cgctggatac tgtggtcaga cagatgagta ttgtgcccct     180

gaaaactgcc aaagccaatg tcgaacccca tctcccccac caccaccacc tccgcccttc     240

acgccaccac ctccggtttc tcccgatgat gttagtcaca tcattacttc ctcgcttttc     300

gagaagatgc tcaaaaatcg aaatgatcct cgatgcaaaa gtaaaggctt ctacacttac     360

gacgccttca taactgctgc tagaaaattt cctggatttg gtactactgg ctctcttgaa     420

actcgtacaa gagaactagc tgcgttcttt ggccaaactt ctcacgaaac cacaggagga     480

tggtcatctg ctgatcaggg aggaccatat gcctggggat attgctatat catagaacaa     540

gatgatcaat ctccgcattg cgtcgacagc ctagaatggc cctgtgttcc tggcgaattc     600

tactatggtc gtggacccat ccagatcagt tag                                  633


<210> SEQ ID NO 10
<211> LENGTH: 210
<212> TYPE: PRT
<213> ORGANISM: Cannabis sativa

<400> SEQUENCE: 10

Met Lys Tyr Ser Tyr Tyr Leu Trp Leu Phe Thr Thr Ile Thr Ala Leu
1               5                   10                  15

Leu Val Val Gly Ile Arg Ser Asn Pro Pro Gly Gly Glu Cys Gly Lys
            20                  25                  30

Gln His Glu Tyr Ala Leu Cys Asp Asp Gly Tyr Cys Cys Ser Asn Ala
        35                  40                  45

Gly Tyr Cys Gly Gln Thr Asp Glu Tyr Cys Ala Pro Glu Asn Cys Gln
    50                  55                  60

Ser Gln Cys Arg Thr Pro Ser Pro Pro Pro Pro Pro Pro Pro Pro Phe
65                  70                  75                  80

Thr Pro Pro Pro Pro Val Ser Pro Asp Asp Val Ser His Ile Ile Thr
                85                  90                  95

Ser Ser Leu Phe Glu Lys Met Leu Lys Asn Arg Asn Asp Pro Arg Cys
            100                 105                 110
```

```
Lys Ser Lys Gly Phe Tyr Thr Tyr Asp Ala Phe Ile Thr Ala Ala Arg
        115                 120                 125

Lys Phe Pro Gly Phe Gly Thr Thr Gly Ser Leu Glu Thr Arg Thr Arg
    130                 135                 140

Glu Leu Ala Ala Phe Phe Gly Gln Thr Ser His Glu Thr Thr Gly Gly
145                 150                 155                 160

Trp Ser Ser Ala Asp Gln Gly Gly Pro Tyr Ala Trp Gly Tyr Cys Tyr
                165                 170                 175

Ile Ile Glu Gln Asp Asp Gln Ser Pro His Cys Val Asp Ser Leu Glu
            180                 185                 190

Trp Pro Cys Val Pro Gly Glu Phe Tyr Tyr Gly Arg Gly Pro Ile Gln
        195                 200                 205

Ile Ser
    210


<210> SEQ ID NO 11
<211> LENGTH: 633
<212> TYPE: DNA
<213> ORGANISM: Cannabis sativa

<400> SEQUENCE: 11

atgaaatact cttattattt gtggctgttc actaccatta cagcattgtt ggtagtagga     60

attaggtcca atcctccagg tggagagtgt ggaaaacaac atgaatatgc tctctgtgat    120

gacggctatt gttgtagtaa cgctggatac tgtggtcaga cagatgagta ttgtgcccct    180

gaaaactgcc aaagccaatg tcgaacccca tctcccccac caccaccacc tccgcccttc    240

acgccaccac ctccggtttc tcccgatgat gttagtcaca tcattacttc ctcgcttttc    300

gagaagatgc tcaaaaatcg aaatgatcct cgatgcaaaa gtaaaggctt ctacacttac    360

gacgccttca taactgctgc tagaaaattt cctggatttg gtactactgg ctctcttgaa    420

actcgtacaa gagaactagc tgcgttcttt ggccaaactt ctcacgaaac cacaggagga    480

tggtcatctg ctgatcaggg aggaccatat gcctggggat attgctatat catagaacaa    540

gatgatcaat ctccgcattg cgtcgacagc ctagaatggc cctgtgttcc tggcgaattc    600

tactatggtc gtggacccat ccagatcagt tag                                 633


<210> SEQ ID NO 12
<211> LENGTH: 346
<212> TYPE: PRT
<213> ORGANISM: Cannabis sativa

<400> SEQUENCE: 12

Met Ala Ser Pro Lys Tyr Gln Ile Gly Tyr Trp Leu Ala Ser Lys Glu
1               5                   10                  15

Lys Leu Phe Ser Ser Glu Asn Lys Ser Ile Val Ser Ser Phe Thr His
            20                  25                  30

Leu Tyr Tyr Ala Phe Leu Gln Val Lys Asn Asp Thr Gly Glu Leu Ile
        35                  40                  45

Ile Pro Pro Glu Leu Glu Asn Asp Met Lys Ser Phe Val Lys Ser Ala
    50                  55                  60

His Asp Asn Gln Lys Lys Ala Leu Val Ser Ile Gly Gly Pro Lys Thr
65                  70                  75                  80

Ser Asp Asp Asn Asp Pro Ser Ser Ala Ile Ser Met Met Ala Lys Ser
                85                  90                  95

Ala Glu Lys Arg Asn Lys Phe Val Glu Ser Thr Leu Ala Phe Ala Lys
            100                 105                 110
```

```
Asp Phe Ser Phe Asp Gly Phe Glu Leu Ala Trp Glu Tyr Pro Lys Thr
        115                 120                 125

Ala Asn Asp Met Arg Asn Leu Ser Asn Leu Phe Asn Ser Trp Lys Ser
    130                 135                 140

Ser Leu Asn Ser Cys Asn Asp Asn Arg Lys Asn Leu Leu Leu Ser Ile
145                 150                 155                 160

Ala Val Tyr Cys Lys Pro Ile Ile Pro Asn Ala Thr Ser Lys Gln Glu
                165                 170                 175

Ile Lys Tyr Pro Ser Glu Leu Glu Asn Tyr Val Asp Ile Phe Asn Ile
            180                 185                 190

Ile Leu Tyr Asn Tyr Cys Pro Val Thr Cys Pro His Ser Gln Phe Lys
        195                 200                 205

Pro Ser Asn Pro Gly Pro Asn Asn Ser Ser Glu Asp Ser Ile Asn Ser
    210                 215                 220

Trp Leu Ala Thr Asn Asp Phe Ser Thr Cys Lys Leu Val Met Gly Ile
225                 230                 235                 240

Pro Leu Tyr Gly Asn Lys Trp Thr Leu Ala Asp Glu Asn Asp Ser Ser
                245                 250                 255

Ile Gly Ala Pro Thr Ile Ala Tyr Ser Gly Pro Ile Ala Tyr Lys Asp
            260                 265                 270

Ile Pro Asp Pro Glu Gly Gly Ile Tyr Asp Lys Asp Val Thr Lys Cys
        275                 280                 285

Met Tyr Lys Ala Asp Lys Asn Thr Trp Tyr Gly Tyr Glu Ala Ser Glu
    290                 295                 300

Ser Ile Asn Glu Lys Val Glu Tyr Ala Lys Lys His Leu Gly Gly Tyr
305                 310                 315                 320

Phe Leu Tyr Ala Ile Gly Asp Asp Asp Asp Gly Gln Thr Met Cys Ile
                325                 330                 335

Ala Ala Ala Glu Gln Met Ala Ala Arg Glu
            340                 345


<210> SEQ ID NO 13
<211> LENGTH: 2127
<212> TYPE: DNA
<213> ORGANISM: Cannabis sativa

<400> SEQUENCE: 13

gcacttgaca tgataagaaa aactctataa atagcatggg atattcaagt gaacaaacac     60

accactacaa aaaacctaat tatatatcat ttttatagtt gtaccatata atggcatctc    120

cgaagtacca aatcggttac tggcttgcat ccaaagaaaa attattttca tctgaaaata    180

agtctattgt atcctcattt actcacctgt attatgcctt tcttcaggtt aaaaatgata    240

ccggagagct gattatccct cccgaacttg agaatgatat gaagtctttt gtcaagagtg    300

ctcatgacaa ccaaaagaaa gctctagtgt ctattggagg cccgaaaaca agcgatgaca    360

atgacccttc ctccgctatc tctatgatgg caaagagcgc tgaaaaacgt aacaagtttg    420

ttgaatcgac cttagctttc gctaaagact ttagctttga tggttttgag cttgcttggg    480

aatatcctaa aacggcaaat gacatgagaa acctaagcaa tctcttcaac agttggaaat    540

cttctttgaa ttcatgtaat gataatagaa agaacctact actctcaatt gcggtttatt    600

gcaaacccat tattccaaat gctacttcga aacaagaaat caaataccct tccgaactcg    660

aaaattatgt tgacattttc aatataatcc tctacaatta ttgtccagtc acttgtccac    720

attcccaatt caagcctagc aaccctggcc ctaataacag cagtgaagac tctattaata    780
```

```
gttggctcgc tacaaatgat ttttcgacct gtaaactagt tatgggcatt cccttgtacg    840
gaaataaatg gacattggct gatgaaaatg attccagcat tggggcacca actattgcct    900
attctggtcc catcgcgtat aaagatattc ctgatccaga aggtgggatc tatgataagg    960
atgttaccaa gtgcatgtac aaggctgata aaaatacttg gtatggctac gaagcttcag   1020
aatctataaa tgaaaaggtc gagtatgcta agaaacatct tggtgggtat ttcctatatg   1080
ccattgggga tgatgatgat ggtcaaacca tgtgtattgc agctgcagag caaatggcag   1140
caagagaatg aagatcttgt tttccaatta tgaatgaggg tggatttaaa tatatttaaa   1200
taacagcaaa gtacacataa aaactttgca ccaataaacc accttgatca cttttatctg   1260
tttttgtatt gtattgtgta ataaattaaa ggcctattcg ttggtccttt tcgtgcaaga   1320
gaggaatctc gaccacctta tcttggtgta agagtaactt cattttgcac tagtacctaa   1380
taagattgtc attgtttgtg tgctttttag ttttatgtgt catgaaataa atgaataagg   1440
attgtgtatc ttttgaagtt tttctttgca taatgttttg ccccttgcac taaaatgaat   1500
gggatgagga aacatgttag catcattaaa gcaaaacaga agaaatagca taattaatat   1560
gaggaatagt ctctggaagc tttattgaat aagtaaaagg agaccaaggt ctcttacata   1620
tattattgta tagcatcaca gatcttgttt tccaattatg aatgagggtg gatttaaata   1680
tatttaaata acagcaaagt acacataaaa actttgcacc aataaaccac cttgatcact   1740
tttatctgtt tttgtattgt attgtgtaat aaattaaagg cctattcgtt ggtccttttc   1800
gtgcaagaga ggaatctcga ccaccttatc ttggtgtaag agtaacttca ttttgcacta   1860
gtacctaata agattgtcat tgtttgtgtg ctttttagtt ttatgtgtca tgaaataaat   1920
gaataaggat tgtgtatctt ttgaagtttt tctttgcata atgttttgcc ccttgcacta   1980
aaatgaatgg gatgaggaaa catgttagca tcattaaagc aaaacagaag aaatagcata   2040
attaatatga ggaatagtct ctggaagctt tattgaataa gtaaaaggag accaaggtct   2100
cttacatata ttattgtata gcatcac                                        2127
```

```
<210> SEQ ID NO 14
<211> LENGTH: 320
<212> TYPE: PRT
<213> ORGANISM: Cannabis sativa

<400> SEQUENCE: 14

Met Lys Ile Cys Ala Leu Thr Ile Val Ser Leu Leu Leu Leu Thr Ile
1               5                   10                  15

Glu Gly Gly Ser Ala Glu Gln Cys Gly Arg Gln Ala Gly Gly Ala Leu
            20                  25                  30

Cys Pro Gly Gly Leu Cys Cys Ser Glu Phe Gly Trp Cys Gly Asn Thr
        35                  40                  45

Pro Asp Tyr Cys Asn Asp Lys Cys Gln Ser Gln Cys Gly Ser Ser Pro
    50                  55                  60

Gly Gly Gly Gly Leu Gly Gly Leu Ile Ser Arg Ala Thr Phe Asp Asn
65                  70                  75                  80

Met Leu Lys His Arg Asn Asp Gly Ala Cys Pro Ala Arg Asn Phe Tyr
                85                  90                  95

Thr Tyr Asp Ala Phe Ile Ser Ala Ala Lys Ala Phe Pro Gly Phe Gly
            100                 105                 110

Asn Thr Gly Asp Asp Ala Thr Lys Lys Arg Glu Ile Ala Ala Phe Leu
        115                 120                 125
```

```
Ala Gln Thr Ser His Glu Thr Thr Gly Gly Trp Pro Thr Ala Pro Asp
    130                 135                 140

Gly Pro His Ser Trp Gly Tyr Cys Phe Val Arg Glu Arg Asn Pro Pro
145                 150                 155                 160

Ser Asp Tyr Cys Arg Ser Asp Ala Thr Tyr Pro Cys Ala Pro Gly Arg
                165                 170                 175

Gln Tyr Tyr Gly Arg Gly Pro Met Gln Leu Ser Trp Asn Tyr Asn Tyr
            180                 185                 190

Gly Gln Cys Gly Arg Ala Ile Gly Val Asp Leu Leu Asn Asn Pro Asp
        195                 200                 205

Leu Val Ala Thr Asp Pro Val Ile Ser Phe Lys Ala Ala Ile Trp Phe
    210                 215                 220

Trp Met Thr Pro Gln Ser Pro Lys Pro Ser Cys His Asp Val Ile Thr
225                 230                 235                 240

Gly Arg Trp Asn Pro Ser Gly Ala Asp Gln Ala Ala Gly Arg Val Pro
                245                 250                 255

Gly Tyr Gly Val Thr Thr Asn Ile Ile Asn Gly Gly Leu Glu Cys Gly
            260                 265                 270

Lys Gly Arg Asn Asp Gln Val Glu Asp Arg Ile Gly Phe Phe Lys Arg
        275                 280                 285

Tyr Cys Asp Ile Phe Arg Ile Gly Tyr Gly Asn Asn Leu Asp Cys Tyr
    290                 295                 300

Asn Gln Arg Pro Trp Gly Asn Gly Leu Phe Gln Leu Asp Ala Val Met
305                 310                 315                 320
```

<210> SEQ ID NO 15
<211> LENGTH: 963
<212> TYPE: DNA
<213> ORGANISM: Cannabis sativa

<400> SEQUENCE: 15

```
atgaagattt gtgcattgac aattgtgtcc ctgctgttgt tgaccataga aggagggtca      60

gcagagcaat gtggaagaca agctgggggt gctctgtgtc caggggggct gtgctgcagc     120

gaatttgggt ggtgtggcaa cacacccgat tactgcaacg ataaatgcca aagccaatgc     180

ggatcaagtc ctgggggtgg gggccttggt ggtctaattt caagggccac ttttgataat     240

atgcttaagc atcgtaacga tggtgcttgt cctgctagaa acttttacac ttacgacgct     300

ttcatctccg ctgctaaagc ttttcctggc ttcggcaaca ctggtgatga tgcaactaag     360

aaaagggaga tcgctgcttt cttagcccaa acttcccacg aaactacagg tggatggcca     420

acggcacctg atggcccaca ttcttgggga tactgcttcg tgagggagcg aaatccacca     480

agcgattact gtagatctga cgctacttac ccttgtgctc ccggaaggca atactatggc     540

cgtggtccaa tgcaactttc atggaactac aactacggac aatgtggaag agccattgga     600

gtggacctac tgaacaatcc agaccttgta gctacggacc ctgtaatttc tttcaaggca     660

gcaatctggt tctggatgac ccccacagtca ccgaagccat cctgccatga cgtcatcacc    720

gggagatgga atccctccgg ggctgatcag gccgccggta gagtccccgg ttacggtgtg     780

acgacgaaca tcatcaacgg cgggcttgag tgcgggaaag gccggaacga tcaggtggaa     840

gaccgaattg ggttctttaa gaggtactgt gatatattcc ggattgggta cggaaataat     900

ttggactgtt acaaccaaag gccttgggga aatggactct tccagctgga tgcggtcatg     960

taa                                                                   963
```

```
<210> SEQ ID NO 16
<211> LENGTH: 365
<212> TYPE: PRT
<213> ORGANISM: Cannabis sativa

<400> SEQUENCE: 16

Met Lys Leu Ser Asn Leu Leu Thr Leu Phe Ser Leu Ser Cys Leu Ser
1               5                   10                  15

Val Leu Leu Val Gly Asn Ile Val Ser Thr Asp Gly Ala Gln Cys Gly
            20                  25                  30

Arg Gln Ala Gly Gly Ala Leu Cys Arg Asn Asn Leu Cys Cys Ser Gln
        35                  40                  45

Trp Gly Phe Cys Gly Ser Thr Glu Ala Tyr Cys Gly Ala Gly Cys Gln
    50                  55                  60

Ser Gln Cys Trp Asn Glu Arg Pro Asp His Arg Cys Gly Ala Gly Thr
65                  70                  75                  80

Gly Asn Ser Pro Cys Ala Pro Gly Arg Cys Cys Ser Arg Phe Gly Phe
                85                  90                  95

Cys Gly Ser Thr Ala Ala Tyr Cys Gln Gly Asn Asn Cys Gln Tyr Gln
            100                 105                 110

Cys Trp Arg Ile Ala Pro Ser Thr Asp Glu Leu Ile Arg Ala Met Leu
        115                 120                 125

Gly Asp Tyr Asn Ala Asn Asp Asp Ser Asp Ile Arg Asn Val Ile Ser
    130                 135                 140

Glu Ser Ile Phe Asn Glu Met Phe Lys His Arg Lys Asp Cys Pro Ser
145                 150                 155                 160

Lys Gly Phe Tyr Asp Tyr Gln Ser Phe Val Ile Ala Ala Ala Ser Phe
                165                 170                 175

Pro Gly Phe Gly Thr Thr Gly Asp Val Ala Thr Arg Lys Arg Glu Ile
            180                 185                 190

Ala Ala Phe Phe Ala Gln Thr Ser His Ala Thr Ala Gly Lys Trp Ile
        195                 200                 205

Asp Ser Phe Asp Gln His Ala Trp Gly Tyr Cys Phe Ile Asn Arg Thr
    210                 215                 220

Ala Gly Glu Tyr Asp Tyr Cys Thr Ser Ser His Trp Pro Cys Ala Ala
225                 230                 235                 240

Gly Lys Lys Tyr Asn Ser Arg Gly Pro Ile Gln Leu Thr His Asn Tyr
                245                 250                 255

Asn Tyr Gly Leu Ala Ser Glu Ala Leu Gly Ile Asp Leu Ile Asn Asn
            260                 265                 270

Pro Glu Leu Val Ala Thr Asp Ser Val Val Ser Phe Lys Thr Ala Val
        275                 280                 285

Trp Tyr Trp Met Thr Gln His Asp Asn Asn Pro Ser Phe His Asn Ile
    290                 295                 300

Val Ile Asn Ala Asn Ser Gly Ile Lys Asn Gln Leu Pro Thr Tyr Ala
305                 310                 315                 320

Asn Thr Asn Asn Asp Lys Asn Leu Val Gly Tyr Tyr Lys Arg Tyr Cys
                325                 330                 335

Asp Met Leu Arg Val Ser Tyr Gly Asp Asn Leu Asp Tyr Leu Ser Lys
            340                 345                 350

Phe Pro Asn Ala Ser Gly Ile Ser Met Leu Ser Gln Ile
        355                 360                 365


<210> SEQ ID NO 17
<211> LENGTH: 1098
```

```
<212> TYPE: DNA
<213> ORGANISM: Cannabis sativa

<400> SEQUENCE: 17

atgaagttaa gcaaccttct tacactcttt tccctttcct gtctttctgt tttgctagtg     60

gggaatattg tctctacaga tggagcccaa tgtggaagac aggcaggcgg ggccttgtgt    120

cgaaataacc tctgttgtag ccaatggggt ttttgtggta gcacagaagc ctattgtgga    180

gctggttgtc aaagtcaatg ttggaatgaa agacctgatc acagatgtgg ggctggcact    240

ggaaacagtc catgcgctcc aggaaggtgt tgtagcagat ttgggttttg tggtagcaca    300

gctgcttatt gccaaggaaa caattgtcaa taccaatgtt ggagaattgc accttccact    360

gatgaactca ttcgtgctat gctcggagat tataacgcca atgatgattc agatataaga    420

aatgttatta gtgaatcaat cttcaacgaa atgtttaagc atagaaagga ttgcccaagt    480

aaaggtttct acgattacca gtcttttgtc attgctgctg cctctttccc tggttttggt    540

accactggag atgtggcaac tcgtaaaagg gaaatcgcag ctttctttgc tcaaacatct    600

catgcaactg caggaaaatg gattgattca tttgatcaac atgcatgggg atattgcttt    660

atcaatagaa ctgctggcga gtatgattat tgtacatctt ctcattggcc atgtgctgct    720

ggcaaaaaat ataatagtcg aggaccaatt caacttaccc acaactacaa ctatgggctt    780

gctagtgaag cactgggaat agatttgata aacaatcctg aattggtagc aacagactca    840

gtggtgtcgt tcaaaactgc cgtatggtat tggatgactc aacatgataa caacccttca    900

ttccacaaca ttgttatcaa tgcaaattct ggaattaaaa accaactccc aacttatgct    960

aataccaata atgacaaaaa ccttgttggg tactataaaa ggtactgtga catgttaagg   1020

gtgagttatg gagataactt agactatttg tctaagtttc ctaacgcctc tggcatttct   1080

atgctttccc agatctga                                                 1098


<210> SEQ ID NO 18
<211> LENGTH: 365
<212> TYPE: PRT
<213> ORGANISM: Cannabis sativa

<400> SEQUENCE: 18

Met Lys Leu Ser Asn Leu Leu Thr Leu Phe Ser Leu Ser Cys Leu Ser
1               5                   10                  15

Val Leu Leu Val Gly Asn Ile Val Ser Thr Asp Gly Ala Gln Cys Gly
            20                  25                  30

Arg Gln Ala Gly Gly Ala Leu Cys Arg Asn Asn Leu Cys Cys Ser Gln
        35                  40                  45

Trp Gly Phe Cys Gly Ser Thr Glu Ala Tyr Cys Gly Ala Gly Cys Gln
    50                  55                  60

Ser Gln Cys Trp Asn Glu Arg Pro Asp His Arg Cys Gly Ala Gly Thr
65                  70                  75                  80

Gly Asn Ser Pro Cys Ala Pro Gly Arg Cys Cys Ser Arg Phe Gly Phe
                85                  90                  95

Cys Gly Ser Thr Ala Ala Tyr Cys Gln Gly Asn Asn Cys Gln Tyr Gln
            100                 105                 110

Cys Trp Arg Ile Ala Pro Ser Thr Asp Glu Leu Ile Arg Ala Met Leu
        115                 120                 125

Gly Asp Tyr Asn Ala Asn Asp Asp Ser Asp Ile Arg Asn Val Ile Ser
    130                 135                 140

Glu Ser Ile Phe Asn Glu Met Phe Lys His Arg Lys Asp Cys Pro Ser
```

```
145                 150                 155                 160

Lys Gly Phe Tyr Asp Tyr Gln Ser Phe Val Ile Ala Ala Ala Ser Phe
                165                 170                 175

Pro Gly Phe Gly Thr Thr Gly Asp Val Ala Thr Arg Lys Arg Glu Ile
            180                 185                 190

Ala Ala Phe Phe Ala Gln Thr Ser His Ala Thr Ala Gly Lys Trp Ile
        195                 200                 205

Asp Ser Phe Asp Gln His Ala Trp Gly Tyr Cys Phe Ile Asn Arg Thr
    210                 215                 220

Ala Gly Glu Tyr Asp Tyr Cys Thr Ser Ser His Trp Pro Cys Ala Ala
225                 230                 235                 240

Gly Lys Lys Tyr Asn Ser Arg Gly Pro Ile Gln Leu Thr His Asn Tyr
                245                 250                 255

Asn Tyr Gly Leu Ala Ser Glu Ala Leu Gly Ile Asp Leu Ile Asn Asn
            260                 265                 270

Pro Glu Leu Val Ala Thr Asp Ser Val Val Ser Phe Lys Thr Ala Val
        275                 280                 285

Trp Tyr Trp Met Thr Gln His Asp Asn Asn Pro Ser Phe His Asn Ile
    290                 295                 300

Val Ile Asn Ala Asn Ser Gly Ile Lys Asn Gln Leu Pro Thr Tyr Ala
305                 310                 315                 320

Asn Thr Asn Asn Asp Lys Asn Leu Val Gly Tyr Tyr Lys Arg Tyr Cys
                325                 330                 335

Asp Met Leu Arg Val Ser Tyr Gly Asp Asn Leu Asp Tyr Leu Ser Lys
            340                 345                 350

Phe Pro Asn Ala Ser Gly Ile Ser Met Leu Ser Gln Ile
        355                 360                 365
```

<210> SEQ ID NO 19
<211> LENGTH: 26
<212> TYPE: DNA
<213> ORGANISM: Cannabis sativa

<400> SEQUENCE: 19
cctccaacaa ctctggtcga aataac 26

<210> SEQ ID NO 20
<211> LENGTH: 22
<212> TYPE: DNA
<213> ORGANISM: Cannabis sativa

<400> SEQUENCE: 20
caccttctgg cctaaccgaa ac 22

<210> SEQ ID NO 21
<211> LENGTH: 24
<212> TYPE: DNA
<213> ORGANISM: Cannabis sativa

<400> SEQUENCE: 21
agcaacgtgg acgggttcaa ctta 24

<210> SEQ ID NO 22
<211> LENGTH: 24
<212> TYPE: DNA
<213> ORGANISM: Cannabis sativa

<400> SEQUENCE: 22
agtcaaactg atagagattg gaac 24

<210> SEQ ID NO 23
<211> LENGTH: 23
<212> TYPE: DNA
<213> ORGANISM: Cannabis sativa

<400> SEQUENCE: 23
tgcaatgtag ttgcaggtgg ttt 23

<210> SEQ ID NO 24
<211> LENGTH: 20
<212> TYPE: DNA
<213> ORGANISM: Cannabis sativa

<400> SEQUENCE: 24
gccaatttct tggcctctac 20

<210> SEQ ID NO 25
<211> LENGTH: 20
<212> TYPE: DNA
<213> ORGANISM: Cannabis sativa

<400> SEQUENCE: 25
tccacagacc caacaacatc 20

<210> SEQ ID NO 26
<211> LENGTH: 20
<212> TYPE: DNA
<213> ORGANISM: Cannabis sativa

<400> SEQUENCE: 26
tagagtcgcc ggaggaatag 20

<210> SEQ ID NO 27
<211> LENGTH: 15
<212> TYPE: DNA
<213> ORGANISM: Cannabis sativa

<400> SEQUENCE: 27
cctccaccgt tgaat 15

<210> SEQ ID NO 28
<211> LENGTH: 40
<212> TYPE: DNA
<213> ORGANISM: Cannabis sativa

<400> SEQUENCE: 28
tacacgacgt tgtaaaacga cccagatgct aactgcacga 40

<210> SEQ ID NO 29
<211> LENGTH: 41
<212> TYPE: DNA
<213> ORGANISM: Cannabis sativa

<400> SEQUENCE: 29
aggataacaa tttcacacag ggacttctcc tgacctgacc a 41

<210> SEQ ID NO 30
<211> LENGTH: 15
<212> TYPE: DNA
<213> ORGANISM: Cannabis sativa

<400> SEQUENCE: 30

-continued gccaaatggt caggt 15

<210> SEQ ID NO 31
<211> LENGTH: 22
<212> TYPE: DNA
<213> ORGANISM: Cannabis sativa

<400> SEQUENCE: 31
cgtgtacggg agctgattat ac 22

<210> SEQ ID NO 32
<211> LENGTH: 20
<212> TYPE: DNA
<213> ORGANISM: Cannabis sativa

<400> SEQUENCE: 32
gggttgttgc tgttgttgtc 20

<210> SEQ ID NO 33
<211> LENGTH: 24
<212> TYPE: DNA
<213> ORGANISM: Cannabis sativa

<400> SEQUENCE: 33
agatactacg ccaacagcag cagg 24